United States Patent
Canaveral et al.

(10) Patent No.: US 7,901,409 B2
(45) Date of Patent: Mar. 8, 2011

(54) INTRAMEDULLAR DEVICES AND METHODS TO REDUCE AND/OR FIX DAMAGED BONE

(75) Inventors: Claudia M. Canaveral, Alameda, CA (US); Lew Samuels, Walnut Creek, CA (US); Diana Villegas, Alameda, CA (US)

(73) Assignee: Canaveral Villegas Living Trust, Alameda, CA (US)

( * ) Notice: Subject to any disclaimer, the term of this patent is extended or adjusted under 35 U.S.C. 154(b) by 755 days.

(21) Appl. No.: 11/336,400

(22) Filed: Jan. 20, 2006

(65) Prior Publication Data
US 2007/0173826 A1    Jul. 26, 2007

(51) Int. Cl.
*A61F 2/46* (2006.01)
*A61F 2/44* (2006.01)

(52) U.S. Cl. .................. 606/86 R; 623/17.11; 600/222; 606/60; 606/90; 606/105

(58) Field of Classification Search .... 623/17.11–17.16; 606/205–208, 198, 90, 86, 63, 105, 86 R, 606/60; 600/220, 222, 225, 206, 210, 213, 600/216, 217, 219, 229
See application file for complete search history.

(56) References Cited

U.S. PATENT DOCUMENTS

| | | | |
|---|---|---|---|
| 3,750,652 A * | 8/1973 | Sherwin | 606/90 |
| 4,205,683 A | 6/1980 | O'Neill | |
| 4,369,772 A | 1/1983 | Miller | |
| 4,969,888 A | 11/1990 | Scholten et al. | |
| 5,108,404 A | 4/1992 | Scholten et al. | |
| 5,549,679 A | 8/1996 | Kuslich | |
| 5,658,310 A | 8/1997 | Berger | |
| 5,776,054 A * | 7/1998 | Bobra | 600/219 |
| 5,827,289 A | 10/1998 | Reiley et al. | |
| 5,891,147 A | 4/1999 | Moskovitz et al. | |
| 5,972,015 A | 10/1999 | Scribner et al. | |
| 6,019,765 A | 2/2000 | Thornhill et al. | |
| 6,019,776 A | 2/2000 | Preissman et al. | |
| 6,033,411 A | 3/2000 | Preissman | |
| 6,039,761 A * | 3/2000 | Li et al. | 623/17.16 |
| 6,048,346 A | 4/2000 | Reiley et al. | |
| 6,066,154 A | 5/2000 | Reiley et al. | |
| 6,174,334 B1 * | 1/2001 | Suddaby | 623/17.11 |
| 6,214,012 B1 | 4/2001 | Karpman et al. | |
| 6,231,615 B1 | 5/2001 | Preissman | |
| 6,235,043 B1 | 5/2001 | Reiley et al. | |
| 6,241,734 B1 | 6/2001 | Scribner et al. | |

(Continued)

FOREIGN PATENT DOCUMENTS

CA         2287112 C        3/2001

(Continued)

OTHER PUBLICATIONS

Website from University of Pittsburgh, "Osteoporosis and Vertebral Compression Fractures".

(Continued)

*Primary Examiner* — Eduardo C Robert
*Assistant Examiner* — Ellen C Hammond
(74) *Attorney, Agent, or Firm* — Quine Intellectual Property Law Group, P.C.; Paul Littlepage

(57) ABSTRACT

The present invention comprises methods and devices for reduction and/or fixation of fractured or diseased bone or for prevention of fracture or collapse of diseased/damaged bone.

18 Claims, 8 Drawing Sheets

U.S. PATENT DOCUMENTS

| | | | |
|---|---|---|---|
| 6,248,110 | B1 | 6/2001 | Reiley et al. |
| 6,251,139 | B1 | 6/2001 | Lin et al. |
| 6,273,916 | B1 | 8/2001 | Murphy |
| 6,280,456 | B1 | 8/2001 | Scribner et al. |
| 6,332,895 | B1 * | 12/2001 | Suddaby .................. 623/17.11 |
| 6,440,138 | B1 | 8/2002 | Reiley et al. |
| 6,582,439 | B1 | 6/2003 | Sproul |
| 6,582,451 | B1 * | 6/2003 | Marucci et al. ............. 606/207 |
| 7,044,971 | B2 * | 5/2006 | Suddaby .................. 623/17.15 |
| 7,056,342 | B2 * | 6/2006 | Michelson ................ 623/17.11 |
| 7,070,598 | B2 * | 7/2006 | Lim et al. ....................... 606/99 |
| 7,297,146 | B2 * | 11/2007 | Braun et al. ................. 606/279 |
| 2002/0068974 | A1 | 6/2002 | Kuslich et al. |
| 2002/0156483 | A1 | 10/2002 | Voellmicke et al. |
| 2002/0161373 | A1 | 10/2002 | Osorio et al. |
| 2003/0018339 | A1 | 1/2003 | Higueras et al. |
| 2003/0032964 | A1 | 2/2003 | Watkins et al. |
| 2003/0050702 | A1 | 3/2003 | Berger |
| 2003/0125746 | A1 | 7/2003 | Sproul |
| 2003/0220648 | A1 | 11/2003 | Osorio et al. |
| 2003/0225416 | A1 * | 12/2003 | Bonvallet et al. ............ 606/105 |
| 2003/0233096 | A1 | 12/2003 | Osorio et al. |
| 2004/0087994 | A1 | 5/2004 | Suddaby |
| 2004/0097930 | A1 | 5/2004 | Justis et al. |
| 2004/0153064 | A1 | 8/2004 | Foley et al. |
| 2005/0010292 | A1 | 1/2005 | Carrasco |
| 2005/0070911 | A1 | 3/2005 | Carrison et al. |
| 2005/0182416 | A1 * | 8/2005 | Lim et al. ....................... 606/90 |
| 2005/0261683 | A1 * | 11/2005 | Veldhuizen et al. ............ 606/61 |
| 2006/0004377 | A1 * | 1/2006 | Keller ............................. 606/99 |

FOREIGN PATENT DOCUMENTS

| | | |
|---|---|---|
| EP | 1 074 231 A1 | 2/2001 |
| EP | 1 074 231 B1 | 2/2001 |
| JP | 05-269160 A2 | 10/1993 |
| JP | 10-286262 A2 | 10/1998 |
| JP | 2002-17760 A2 | 1/2002 |
| WO | WO 98/56301 A1 | 12/1998 |
| WO | WO 99/18865 A1 | 4/1999 |
| WO | WO 99/18866 A1 | 4/1999 |
| WO | WO 99/62416 A1 | 12/1999 |
| WO | WO 00/09024 A1 | 2/2000 |
| WO | WO 01/76514 A2 | 10/2001 |
| WO | WO 02/30338 A1 | 4/2002 |
| WO | WO 02/34148 A3 | 5/2002 |
| WO | WO 02/43628 A1 | 6/2002 |
| WO | WO 02/064062 A2 | 8/2002 |
| WO | WO 02/085227 A1 | 10/2002 |
| WO | WO 03/007853 A1 | 1/2003 |
| WO | WO03003951 A1 * | 1/2003 |
| WO | WO 2005/016193 A1 | 2/2005 |

OTHER PUBLICATIONS

Alvarez et al. (2003 )"Vertebroplasty in the treatment of vertebral tumors: postprocedural outcome and quality of life," *Eur Spine J.*, 12(4):356-360.

Augat et al, (2005 ) "Mechanics and mechano-biology of fracture healing in normal and osteoporotic bone," *Osteoporos Int.* 16 Suppl 2:S36-43.

Burton et al. (2005) "Vertebroplasty and Kyphoplasty: a Comprehensive Review" *Neurosurg Focus*, 18(3).

Choe et al. (2004) "Pulmonary embolism of polymethyl methacrylate during percutaneous vertebroplasty and kyphoplasty," *AJR Am. J. Roentgenol.*, 183(4):1097-1102.

Cortet et al. (2002 ) "Evaluation of spinal curvatures after a recent osteoporotic vertebral fracture," *Joint Bone Spine*, 69(2):201-208.

Deen et al. (2005 ) "Balloon Kyphoplasty for Treatment of Sacral Insufficiency Fractures. Report of Three Cases," *Neurosurg Focus*, 18(3).

Deen et al. (2005) "Preliminary Results of Balloon Kyphoplasty for Vertebral compression Fractures in Organ Transplant Recipients," *Neurosurg Focus*, 18(3).

Deramond et al. (1997) "Percutaneous Vertebroplasty," *Sem. Musculoskelet Radiol*, 1(2):285-296.

Doetsch, et al. (2004)"The effect of calcium and vitamin D3 supplementation on the healing of the proximal humerus fracture; a randomized placebo-controlled study," *Calcif Tissue Int.*, 75(3):183-188.

FDA Clinical Trial Considerations: Vertebral Augmentation Devices to Treat Spinal Insufficiency Fractures, Oct. 24, 2004, 14 pages.

FDA, P.H.W.N.; Complications Related to the Use of Bone Cement and Bone Void Fillers in Treating Compression Fractures of the Spine, Oct. 31, 2002, 4 pages.

Feltes et al. (2005) "Immediate and Early Postoperative Pain Relief After Kyphoplasty Without Significant Restoration of Vertebral Body Height in Acute Osteoporotic Vertebral Fractures," *Neurosurg Focus*, 18(3).

Gaitanis et al. (2004)"Balloon kyphoplasty for the treatment of pathological vertebral compressive fractures," *Eur Spine J.*, 14(3):250-260.

Gerszten et al. (2005) "Combination Kyphoplasty and Spinal Radiosurgery: a New Treatment Paragidm for Pathological Fractures," *Neurosurg Focus*, 18(3).

Harrop et al. (2004) "Primary and secondary osteoporosis' incidence of subsequent vertebral compression fractures after kyphoplasty," *Spine*, 29(19): 2120.

Lam et al. (2005) "A Novel Percutaneous System for Bone Graft Delivery and Containment for Elevation and Stabilization of Vertebral Compression Fractures," *Neurosurg Focus*, 18 (3).

Leferink et al. (2003) "Burst fractures of the thoracolumbar spine: changes of the spinal canal during operative treatment and follow up," *Eur. Spine J.*, 12(3):255-260.

Liu, et al. (2004)"Surgical management of cervical spinal metastasis: anterior reconstruction and stabilization techniques," *Neurosurg Clin N Am.*, 15(4):413-424.

Melton (1997) "Epidemiology of spinal osteoporosis," *Spine*, 22(24 Suppl.):2S-11S.

Polikeit et al. (2003) "The importance of the endplate for interbody cages in the lumbar spine," *Eur. Spine J.*, 12(6):556-561.

Predey et al. (2002) "Percutaneous Vertebroplasty: New Treatment for Vertebral Compression Fractures," *Am Fam Physician*, 66:611-615, 617.

Rose et al. (2005) "Ex-vivo-Gentherapie mit BMP4 bei kritischen Substanzdefekten und Frakturen im osteoporotischen Tiermodell," (i.e. "Model based on ex vivo gene therapy using (BMP) 4"), *Unfallchirurg*, 108(1):25-34.

Spivak et al. (2005) "Percutaneous Treatment of Vertebral Body Pathology," *J Am Acad Orthop Surg*, 13:6-17.

Starr et al. (1992) "Junctional burst fractures," *Spine*, 17(5):551-557.

The-Gray Sheet, Blue Cross TEC Critiques Kyphoplasty: Kyphon Trial To Address Concerns, in The Gray Sheet. 2005. p. 16.

Verlaan et al (2005) "Balloon Vertebroplasty in Combination With Pedicle Screw Instrumentation: A Novel Technique to Treat Thoracic and Lumbar Burst Fractures," *Spine*, 30(3):E73-E79.

* cited by examiner

INTRAMEDULLAR DEVICES AND METHODS TO REDUCE AND/OR FIX DAMAGED BONE

FIELD OF THE INVENTION

The current invention relates to the field of medical devices. More specifically, the present invention provides devices and methods for intramedullar reduction and fixation of fractured and/or diseased bone and for prevention of fracture or collapse of diseased/damaged bone.

BACKGROUND OF THE INVENTION

Numerous medical conditions can lead to weakened or softened bones in subjects, e.g., osteoporosis, tumors, etc. Such weakened bones can fracture more easily than healthy bones, especially in response to mechanical stress. Compression fractures of the spine are a common example of such damage.

A number of less than satisfactory treatments currently exist to treat fractures of irregular bones, such as vertebral compression fractures, or fractures of the metaphyseal portion of long bones resulting from damaged and/or diseased bone. For example, for vertebral compression fractures bone cement can be injected into the damaged vertebral body, sometimes within a cavity formed within the bone. Alternatively, and/or additionally, support devices that act at a distance from the fractured/diseased bone (e.g., external to the spinal column) can be implanted or used within a subject to act as stabilizers. However, such current methods are unsatisfactory for a number of reasons. For example, bone cement can leak outside of its intended area and can also prevent healing of bone tissue. Current external stabilizing devices usually involve highly invasive surgery and, if promoting fusion between spinal segments, can result in limited range of motion of the spine and promote degenerative changes both above and below the treated level, thus having a negative impact in quality of life for the subject.

Thus, there is a need for better, more anatomical methods and treatments of damaged/diseased bone to prevent and/or promote fracture healing. The current invention provides these and other benefits which will be apparent upon examination of the current specification, claims, and figures.

SUMMARY OF THE INVENTION

In various aspects herein, the invention comprises methods of reducing one or more bone surfaces to a desired position in a subject. Such methods comprise introducing one or more Intramedullar Reduction/Fixation Device (IRFD) into the medullar cavity of a bone via one or more openings (e.g., holes drilled through the cortical bone, fractures/openings in the bone, fractures/openings in the bone that are enlarged by surgeons, etc.) wherein the bone comprises the bone surfaces that are to be reduced/moved/etc. and manipulating the IRFD within the medullar cavity of the bone so that the IRFD contacts the bone surfaces and moves them, thereby reducing the bone surfaces to the desired positions. In some such embodiments the IRFD is left within the bone as an implant to support and/or stabilize the one or more bone surfaces, e.g., until healing is achieved (or optionally for shorter or longer periods or permanently), thereby fixing the one or more bone surfaces.

In other various aspects herein, the invention comprises methods of reducing and fixing one or more bone surfaces to a desired position in a subject. Such methods comprise introducing one or more IRFD into the medullar cavity of a bone via one or more openings (e.g., holes drilled through the cortical bone, fractures/openings in the bone, fractures/openings in the bone that are enlarged by surgeons, etc.) wherein the bone comprises the surfaces to be reduced and fixed and manipulating the IRFD within the medullar cavity of the bone so that the device contacts the bone surfaces and moves them, thereby reducing the bone surfaces to desired positions and leaving the IRFD within the bone to support and/or stabilize them once the bone surfaces are reduced, thereby reducing and fixing the one or more bone surfaces to a desired position.

In the various embodiments of the aspects herein, the bones to be treated with the methods and devices can be fractured bones and/or diseased bones (e.g., vertebra having VCF, etc.), or bones that are susceptible to fracture and/or disease (e.g., in a subject having a disease, such as osteoporosis, causing bone weakening). In certain embodiments, the bones to be treated with the methods/devices of the invention can be those anatomically classified as irregular bones (e.g., spinal vertebra) and/or the metaphyseal portion of long bones, flat bones, and others.

In the various embodiments herein, the devices used in the methods comprise a first contact area (which touches a first bone surface, e.g., the inner surface of a cortical bone facing the cancellous space of the bone) and at least a second contact area (which touches a second bone surface). In certain embodiments, the devices comprise a first arm (which comprises the first contact area) and at least a second arm (which comprises the second contact area). In yet other embodiments, the devices used in the methods comprise one or more continuous flexible or articulated strap which comprises the first and at least second contact areas.

The devices used herein can comprise and/or be composed of one of more of: high-density polyethylene (HDPE), polyetheretherketone (PEEK), metal, stainless steel, titanium, silver, or plastic. The devices herein can also optionally comprise one or more coatings, which can comprise one or more of: bone morphogenetic protein (BMP), hydroxyapatite, silver, a silver containing compound, calcium sulfate, a calcium containing compound, an antibacterial material, an antifungal material, or calcium carbonate.

In certain embodiments, holes created or utilized in bone in which the devices of the invention are inserted can comprise from about 4 mm to about 20 mm in diameter; from about 4 mm to about 15 mm in diameter; from about 4 mm to about 10 mm in diameter; from about 5 mm to about 10 mm in diameter; from about 5 mm to about 7 mm in diameter; from about 5.5 mm to about 6.5 mm in diameter; about 6.5 in diameter; or about 6 mm in diameter depending, e.g., on the bone treated, the size of the device(s) to be inserted, etc. Such openings can comprise various shapes/outlines, e.g., round, square, rectangular, irregular, etc. (all optionally comprising one or more points, or other shapes, on the outline of the opening). Furthermore, in particular embodiments, manipulation of the devices herein does not create open space within the medullar cavity of the bone substantially beyond the space that will be occupied by the implant itself; nor do the methods comprise use of a balloon or balloon device (e.g., to create open space within the interior of bone).

In certain embodiments, the methods of the invention utilize RFD which comprise a first flexible blade and a parallel second, matching flexible blade (each having a proximal end and a distal end with the proximal end of each blade attached to a hollow extender tube having a lumen); a hinged two-armed cross bar, one end of which is attached to the first blade and one end of which is attached to the second blade at attachments points in between the proximal and distal ends of each blade; an extension rod having a proximal end and a distal end which is attached at the distal end to the hinge of the two-armed cross bar and whose proximal end can move through the lumen of the hollow extender tube; and optionally an anchor and/or anti-rotation mechanism or optionally a head/cap that is attached to the hollow extender tube. In such methods, the distal ends of the flexible blades of the IRFD can be moved controllably apart from one another by manipulation of the extension rod and optionally can be locked at one or more desired positions. The methods herein can also comprise any of the various IRFD device embodiments herein. Proximal herein and throughout the specification and claims, e.g., as used in description of an IRFD or IRFD component, refers to the end of an IRFD that is closest to its insertion site into a bone and to the head area (i.e., which stays on the exterior of the bone). Distal refers to an end of an IRFD that is furthest from the entry or insertion point into the bone (i.e., furthest from the head area on the exterior of the bone).

In other aspects, the invention comprises devices for reducing and/or fixing one or more bone surfaces at desired positions, which devices comprise a first flexible blade and a parallel second flexible blade (each having a proximal end and a distal end, the proximal end of each attached to a hollow extender tube having a lumen), a hinged two-armed cross bar, one end of which is attached to the first blade and one end of which is attached to the second blade at attachment points in between the proximal and distal ends of each blade; an extension rod having a proximal end and a distal end which is attached at its distal end to the hinge of the two-armed cross bar and whose proximal end can move through the lumen of the hollow extender tube; and optionally an anchor and/or anti-rotation mechanism or optionally a head/cap that is attached to the hollow extender tube. In such devices the distal ends of the flexible blades can be moved controllably apart from one another by manipulation of the extension rod and optionally can be locked at one or more desired positions.

In particular embodiments, the devices herein have blades that comprise contact areas which touch the bone surfaces (such as surfaces of vertebral bones or bones classified as irregular bones or bone surfaces of metaphyseal portions of long bones, flat bones or any other bones). In certain embodiments the bone surfaces are cortical bone, endplates, or other bone surfaces capable of sustaining a reduction force. In various embodiments, the blades have rounded or blunt distal ends and/or are flexible over less than their entire length(s).

In various embodiments, the extension rod of the devices herein can be manipulated to cause the hinged crossbar to move the distal ends of the blades away from one another or to move the distal ends of the blades towards one another.

In some embodiments, the extension rod comprises a screw mechanism (typically comprising the proximal end of the extension rod). In such embodiments, turning a rotator or nut/ring/cap/hub or other similar mechanism (sometimes referred to collectively herein as a rotator) on the screw moves the extension rod which manipulates the hinged crossbar, which thereby moves the distal ends of the flexible blades.

In certain other embodiments, the extension rod comprises a ratcheted rod having a plurality of teeth on two opposing sides and two opposing flattened (smooth) sides (with no teeth); and a pawl from each flexible blade operatively fitted to the teeth on the rod wherein the pawl from one blade is fitted to the teeth on one side of the rod and the pawl of the other blade fitted to the teeth on the opposing side of the rod. In some such embodiments, the extension rod is manipulated via a removable rod which is optionally pulled, pushed, and/or turned to manipulate the extension rod, thereby moving the hinged crossbar and thereby moving the distal ends of the flexible blades. In such embodiments, the extension rod comprises a swivel device allowing rotation of at least a portion of the proximal end of the extension rod.

In various embodiments of the current invention, the devices are composed of one or more of: HDPE, PEEK, metal, stainless steel, titanium, silver, or plastic. Also in various embodiments, the devices comprise one or more coatings, which can be one or more of: BMP, hydroxyapatite, silver, a silver containing compound, calcium sulfate, a calcium containing compound, an antibacterial material, an antifungal material, or calcium carbonate.

The devices of the current invention can be inserted into one or more bones through openings made by holes drilled or cut through cortical bone (such holes/openings can be entirely manmade or can be enlargements of naturally occurring fractures/holes/breaks). Such holes can be from about 4 mm to about 20 mm in diameter; from about 4 mm to about 15 mm in diameter; from about 4 mm to about 10 mm in diameter; from about 5 mm to about 10 mm in diameter; from about 5 mm to about 7 mm in diameter; from about 5.5 mm to about 6.5 mm in diameter; about 6.5 in diameter; or about 6 mm in diameter. In some embodiments, the devices can be inserted through fractures, breaks, or other non-manmade openings in bones. The openings can comprise various shapes, e.g., round, square, rectangular, irregular, etc. (all optionally comprising one or more points or other shapes on the outline of the opening).

In various embodiments, the devices of the invention do not create open spaces within the medullar areas of the bones in question. In other words, the cancellous matter within the bones is not compressed to create a cavity within the bone that would be substantially greater than the area needed to insert and position the devices of the invention. Thus, in some embodiments, the devices do not create an open space within the medullar cavity of the bone greater than the space utilized by the implant itself. In other embodiments, the devices/methods herein do not create open space of greater than about 2% of cancellous space within the bone, greater than about 5% of cancellous space within the bone, greater than about 10% of cancellous space within the bone, greater than about 15% of cancellous space within the bone, or greater than about 20% of cancellous space within the bone. In yet other embodiments, a device herein creates an open space that is less than 5%, less than 10%, less than 15%, less than 25%, less than 50%, less than 75%, less than 100%, less than 125%, less than 150%, or less than 200% greater than the space occupied by the device itself.

In typical embodiments, the devices do not comprise a balloon or balloon device.

These and other features of the invention will become more fully apparent when the following detailed description is read in conjunction with the accompanying figures.

DETAILED DESCRIPTION

Figure 1A:
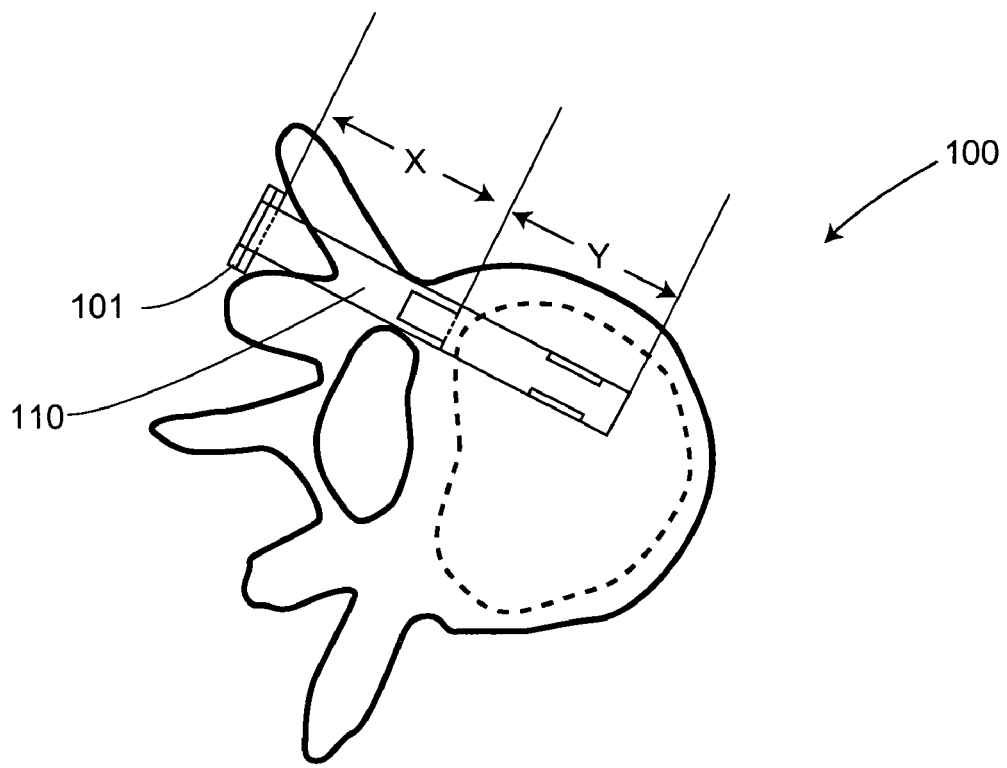
FIG. 1, Panels A and B, displays diagrams showing possible placement locations of various embodiments of IRFDs of the invention (pedicle placement in Panel A and anterior placement in Panel B).

The present invention comprises methods for treatment of fractured/damaged bone and mechanical devices that can be implanted within a medullar cavity of a bone for the treatment of fractures/damage, e.g., resulting from pathological, traumatic, or combined origin. The invention also comprises methods and devices to provide structural reinforcement when collapse of a bone is anticipated or possible, e.g., in conditions such as osteoporosis, tumors, and the like. Even though in certain embodiments the invention is directed towards treatment of bones of the vertebral column, it will be appreciated that the methods and devices herein are capable of use in treatment of other bones as well, e.g., metaphyseal portions of long bones. In certain embodiments, devices herein can be inserted into a vertebra either through the pedicle or through the anterior wall of the vertebra (or through any other aspect of the bone), either open or endoscopically, with their placement within the bone guided fluoroscopically or otherwise.

In particular embodiments, the devices herein (typically referred to as Intramedullar Reduction and Fixation Devices or IRFDs) are inserted into a vertebral body, or other fractured or collapsed bone needing repair or within bones susceptible to damage/collapse. The devices reduce the fractured/collapsed bone and are often oriented to have one or more portions of the device placed against the closest endplate or cortical bone (i.e., from the inside of the bone), and one or more different portions directed to another (e.g., an opposing) endplate or cortical bone in order to reduce and/or support the bone (or bone pieces) in the desired positions. The device can then be left in place for any length of time (including permanently) to provide structure and support to the bone and, optionally subsequently removed if deemed necessary. Several IRFDs can be used to reduce a fracture and each can be implanted from any portal accessible. As will be appreciated, depending on the fracture configuration and/or the bone in question, two or more devices can be used to achieve the desired result, e.g., reduction and fixation of the bone surface(s). The device can be constructed of different metal alloys, ceramics, or plastics or combinations thereof. Furthermore, bio-absorbable materials can be used to construct the device, or in conjunction with the device, or the device can be coated with substances such as drugs or biologics that can stimulate bone healing and/or prevent/treat infection While the devices and methods herein can optionally be used in a number of procedures, the invention typically does not desire or attempt to create cavities within bones that are greater than the space required for the devices and their placement and orientation within the bone. Neither is it typically designed to be used as a vehicle or delivery aid for bone cement.

The devices herein are implants and, in particular embodiments, are not removed until after fracture consolidation or bone healing is achieved. However, in other embodiments, the devices can be left in place even after consolidation or bone healing has occurred. In yet other embodiments, the devices can be used as fracture reduction tool(s) only. In such cases the final treatment of the fracture can be achieved through other means. Thus, the current invention can comprise embodiments wherein the devices are left within a bone for any desired length of time including permanently. The present methods of intramedullar reduction and fixation and the devices facilitating such procedures represent a new approach to the treatment and reinforcement of weakened, diseased and/or fractured bone.

Before describing the present invention in detail, it is to be understood that the invention herein is not limited to particular compositions or biological systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the context clearly dictates otherwise. Thus, for example, reference to "a vertebra" optionally includes a combination of two or more vertebra, and the like.

A "subject" as used herein should be understood to refer to an individual e.g., a human, a mammal, a non-human primate, an equine, a bovine, a canine, etc. that is in need of treatment for a bone fracture or bone damage, or that is in need of treatment to stabilize a bone that is subject to fracture or damage, or to prevent fracture or damage to a bone.

"Reducing" a bone, bone fragment, or bone surface refers to movement or alignment of such bones, bone fragments, or bone surfaces to a desired orientation and location, typically the anatomical positions such bones/fragments/surfaces occupied before bone damage or injury occurred. Depending on context, such action can be referred to as "reduction." Reducing/reduction done by the devices/methods herein in treatment of bones can occur in conjunction with reduction from traditional surgical techniques such as traction, etc.

"Fixing" a bone, bone fragment, or bone surface refers to stabilization and/or substantial immobilization of such bone, bone fragment, or bone surface in a desired orientation and location, typically the anatomical positions such bones/fragments/surfaces occupied before bone damage or injury occurred. Fixing can also optionally include stabilization of bone/fragments/surfaces in a current position in order to prevent unwanted movement or misalignment prior to any actual unwanted movement, etc.

Causes of Bone Weakening and Fracture.

A number of medical and traumatic conditions can lead to weakening of bones, e.g., vertebra, which, in turn, can lead to fracture or collapse of the bone. For example, metabolic bone diseases, such as osteoporosis, osteomalacia, and various tumors or tumor-like conditions are usually associated with osteopenia, or soft skeleton, especially in the elderly patient. Under these conditions bones become brittle which impairs their ability to withstand the various stresses experienced by an individual during normal activities or minor trauma. Even though osteoporosis is the most common cause of bone weakening, other conditions such as benign or malign tumors can also negatively impact bone's ability to handle mechanical stress. Unfortunately, losses in bone strength are often difficult to discover until bone integrity has already been seriously compromised. Without proper screening, the effects of structural failure of the bone at microscopic levels are often not discovered until after a bone fracture has already occurred, at which time much of a subject's overall bone strength has typically weakened to dangerous levels.

Severe osteoporosis can cause compression fractures in the spine (also known as Vertebral Compression Fractures (VCF) as well as hip fractures, wrist fractures, and fractures of other bones. When the vertebral body in the spine collapses from VCF, it causes severe pain, deformity, and loss of height, all of which can severely impact a subject's quality of life. Fractures are the most common problem associated with osteoporosis and despite advances in prevention and treatment, the number of fractures continues to increase. VCF occurs in more than 700,000 patients each year in the United States, more frequently than hip fractures, and often results in prolonged disability. See, e.g., Melton, "Epidemiology of spinal osteoporosis" *Spine*, 1997, 22(24 Suppl.):2S-11S. Vertebral fractures in osteoporotic patients can even occur with minimum trauma or with no trauma at all.

Fractures such as VCF often result in chronic pain with various degrees of intensity. Fragments of the fractured vertebra can cause impingement of nerve roots and even of the spinal cord. Such impingement can produce negative neurological consequences. In addition, the wedging resulting from the fracture can cause progressive spinal deformity such as increased thoracic kyphosis, decreased lumbar lordosis, scoliosis or combinations of such. These different deformities typically compromise the respiratory function of the subject due to a decrease in the size of the thoracic cavity and can lead to impairment of gastrointestinal function as a result of decrease in the size of the abdominal cavity.

VCF, if the patient is neurologically intact, is often treated conservatively until the fracture heals. However, the final result is often an angular deformity of the spine. As an alternative to reducing such fractures, the spine can be fused, a situation that is considered less than ideal. Trauma to other bones besides vertebra also can lead to fractures in which restoring the position of fragments is not possible without a large disruption of the "fracture environment." Closed methods of reduction can produce good results in the short term, but with time, the proper reduction can be lost and the patient ends up with undesirable deformity. Such fractures can include, for instance, those of the tibial plateau and those of the tibial plafond. Restitution of the anatomy and maintenance of such restitution until healing occurs is necessary for a good result.

While many of the illustrations herein focus on use of the current invention in treatment of VCF and related vertebral injuries, it is to be understood that the current invention is not necessarily limited to those embodiments. Those of skill in the art will appreciate that the methods and devices herein are applicable to a number of other bone fractures and conditions, e.g., tibial fractures, etc.

Fracture Repair

Fracture repair, which aims at regaining the functional competence of a bone, is a complex and multifactorial process. For the success of fracture repair, biology and mechanics are both of importance. It is desirable that the biological and mechanical environments be compatible with the processes of cell and tissue proliferation and differentiation. The biological environment is characterized by the vascular supply and by numerous biochemical components. A good vascular supply is a prerequisite for the initiation of the fracture repair process. The biochemical setting involves complex interactions among local and systemic regulatory factors such as growth factors or cytokines. The mechanical environment is determined by the local stress and strain within the fracture. However, in the fractured bone, the local stress and strain is not accessible, and the mechanical environment, therefore, is defined by global mechanical factors (e.g., distance and movement of bone fragments). Moreover, there is considerable interaction between biological factors and mechanical factors, creating a biomechanical environment for the fracture healing process. The biomechanical environment is characterized by osteoblasts and osteocytes that sense the mechanical signal and express biological markers, which affect the repair process. The appropriate combination of the aforementioned factors generates a callus which is new bone that provides stability to the fractured bone with restitution of its mechanical and biological properties.

Traditional VCF Treatment Regimes

Traditional treatment alternatives for VCF are limited to pain management with medications, temporary bed rest, reduced activity, corsets, radiation therapy, injection of polymethylmethacrylate (PMMA) (see description of vertebroplasty and kyphoplasty below), or a combination of the above, all with less than satisfactory results. In addition, to limit further loss of bone, many subjects are prescribed with hormones (e.g., calcitonin), alendronates, vitamins and minerals. Due to co-morbid conditions, many of these subjects are not good candidates for major operations such as internal fixation (with or without reduction of the fracture), usually aimed at obtaining fusion between two or more spinal segments.

Vertebroplasty has been shown to reduce some pain associated with vertebral compression fractures. Nonetheless, its risks are well documented and will be well know by those of skill in the art. In addition to the basic risk of injecting PMMA, there is no control of the flow of PMMA. During injection of PMMA into a fractured vertebral body the cement follows the path of least resistance, which is typically the space between fragments. Some clinicians, in an attempt to have better flow of the cement into the bone, dilute the cement, thus making the risk of leakage even higher. Also, attempts to increase the flow of cement by adding additional liquid monomer to the cement mix increases the amount of unpolymerized or free monomer, which increases the risk for this monomer to reach the bloodstream and cause complications. In a recent study it was found that 72.5% of vertebroplasty procedures resulted in leakage of the cement outside the vertebral body. See Cortet, et al., "Percutaneous vertebroplasty in patients with osteolytic metastases or multiple myeloma" *Rev. Rhum. Engl. Ed.*, 1997, 64(3):177-83. Vertebroplasty does not even attempt at restoring the anatomy. It essentially is used as a symptomatic treatment leaving the vertebral body as collapsed as it was prior to the injection of the cement.

Kyphoplasty refers to the insertion of an expandable body (typically a balloon or balloon-like structure) in a fractured or weakened bone, which is then expanded within the bone. This procedure compresses the cancellous bone, purportedly reducing the fracture, and creating a cavity within the bone that can be filled with a settable material such as PMMA or any number of synthetic bone substitutes. While during kyphoplasty the injected PMMA is less likely to leak out of the vertebral body, there are still a number of problems associated with the procedure For example, the kyphoplasty procedure requires a greater number of surgical tools than a vertebroplasty, thus incurring a greater cost. Moreover, kyphoplasty tools are typically larger in diameter and thus often require larger incisions and are generally more invasive.

Kyphoplasty efforts to reduce fractures result in the expandable body or balloon being placed almost randomly on the endplates of the vertebrae so the resulting PMMA mass will also be randomly placed, thus facilitating loss of any correction achieved (i.e., loss of the proper reduction). The support provided is usually towards the middle line and away from where the majority of the forces are transmitted (i.e., the extremes of the endplates). See Polikeit, et al., "The importance of the endplate for interbody cages in the lumbar spine" *Eur. Spine J.*, 2003, 12(6):556-61.

Use of Bone Cement and Bone Void Fillers

As explained above, PMMA can be injected into a vertebral body with or without the use of balloons or other devices. Such injection purportedly improves the pain and, in some cases, restores some of the lost vertebral height of subjects with VCF. Nonetheless, there are numerous reports of complications with the use of this technique, e.g., pulmonary embolism (see, e.g., Choe, et al., "Pulmonary embolism of polymethyl methacrylate during percutaneous vertebroplasty and kyphoplasty" *AJR Am. J. Roentgenol.*, 2004, 183(4):

1097-102) and cement leakage (see, e.g., Gaitanis, et al., "Balloon kyphoplasty for the treatment of pathological vertebral compressive fractures" *Eur Spine J,* 2004, 14(3):250-260; FDA, Clinical Trial Considerations: Vertebral Augmentation Devices to Treat Spinal Insufficiency Fractures, 2004; and Cortet, et al., "Percutaneous vertebroplasty in patients with osteolytic metastases or multiple myeloma" *Rev Rhum. Engl Ed,* 1997, 64(3): 177-83).

According to the FDA, leakage of bone cements can result in soft tissue damage as well as nerve root pain and compression. Other complications reported with the use of bone cements in the spine include pulmonary embolism, respiratory and cardiac failure, abdominal intrusions/ileus, and death. Each of these types of complications has been reported in conjunction with use of such products in both vertebroplasty and kyphoplasty procedures.

Reported complications associated with the use of bone void fillers, besides bone cement, in the spine include pulmonary embolism, respiratory and cardiac failure, and death. Bone void fillers are cleared for use only in non load bearing applications which greatly limits their use in spinal injuries. Under ideal conditions, these bone void fillers are intended to resorb over time and be replaced with new bone growth. Bone growth in osteoporotic patients or in load bearing applications (e.g. a vertebral compression fracture) has not been adequately studied. See FDA, P.H.W.N., Complications Related to the Use of Bone Cement and Bone Void Fillers in Treating Compression Fractures of the Spine (2002).

Reduction/Fixation of Damaged Bone with IRFDs

The IRFDs of the invention allow restoration of the anatomy of different bones including, but not limited to, vertebrae, tibia, the metaphyseal portions of long bones, etc. Such restoration includes movement of the bone (or bones or bone pieces or bone surfaces) to a desired point and optionally support of the bones in response to pressure loads as the fracture heals. Without being limited to a particular mode of action, the biological principals behind use of IRFDs involves ligamentotaxis and the mechanical principles of structural reinforcement. The IRFDs of the invention are thought to enhance fracture consolidation by favoring the proliferation of biological and biochemical fracture-healing factors, as well as use materials with low elasticity modules to facilitate the sharing of mechanical loads between bone and implant.

In certain embodiments, the IRFDs ensure insertion in a minimally invasive procedure in order to avoid risks and complications of open surgery. When used for the treatment of VCF, the design allows the IRFDs to be placed so that the reduction forces are away from the weakest part of the endplates and will not require the injection of PMMA within the treated bone. The IRFD can eliminate the need for injecting cement or other bone fillers within the bone, which impairs fracture healing and brings well-known adverse events. See above.

The IRFDs of the invention take advantage of the fact that osteoporotic bone has the ability to heal if provided appropriate conditions. See, e.g., Rose, et al., [Treatment of critically sized defects and enhancement of fracture healing in an osteoporotic animal model based on ex vivo gene therapy using (BMP) 4.], *Unfallchirurg,* 2005, 108(1):25-34, and Doetsch, et al., "The effect of calcium and vitamin D3 supplementation on the healing of the proximal humerus fracture: a randomized placebo-controlled study" *Calcif Tissue Int,* 2004, 75(3):183-8. Traditional treatment alternatives have often wrongly assumed that fractures, especially VCFs, will not heal or that fracture healing is not a priority. Such assumptions lead to, e.g., injecting bone cement within the medullar cavity. However, as discussed, such practice not only impairs the biological options of fracture healing by taking the space needed for the bone to grow, but also alters the biological and mechanical conditions necessary for fracture healing. See, e.g., Augat, et al., "Mechanics and mechano-biology of fracture healing in normal and osteoporotic bone" *Osteoporos Int,* 2005, 16 Suppl 2:S36-43. The current invention greatly minimizes the amount of open space created within the cancellous areas, thus leaving more natural tissue to aid in bone healing.

Moreover, the inclusion of an irregular rigid piece of material with elastic properties that are quite different from those of the healthy or diseased bone (e.g., as happens with injection of PMMA or similar fillers) can result in increased bone resorption as it will take away the mechanical load from the bone, which is the main physiological stimulus for bone formation, and cause unevenly distributed stress raisers. See, e.g., Treharne, "Review of Wolf's Law and its proposed means of operation" *Ortho. Rev.,* 1981, 10:25. While injection of PMMA has been widely used and is an accepted technique as a palliative for bone tumors and metastatic lesions that are not expected to heal, (see, e.g., Deramond, et al., "Percutaneous Vertebroplasty" *Semin Musculoskelet Radiol,* 1997, 1(2):285-296; Liu, et al., "Surgical management of cervical spinal metastasis: anterior reconstruction and stabilization techniques" *Neurosurg Clin N Am,* 2004, 15(4):413-24; and, Alvarez, et al., "Vertebroplasty in the treatment of vertebral tumors: postprocedural outcome and quality of life" *Eur Spine J,* 2003. 12(4):356-60) it is a poor treatment option that is maintained by the lack of better alternatives for osteoporotic/osteopenic bone or the like.

The methods and devices of the current invention not only favor the healing process by avoiding the use of PMMA and other fillers but also provide structural reinforcement to the fractured/diseased bone. By using osteo-conductive biomaterials in certain embodiments, the IRFD can support the process of fracture healing and maintain the results necessary to avoid the progression of thoracic kyphosis and/or loosing of lumbar lordosis and its deleterious clinical consequences. See, Cortet, et al., "Evaluation of spinal curvatures after a recent osteoporotic vertebral fracture" *Joint Bone Spine,* 2002, 69(2):201-8.

The IRFDs herein optionally provide, inter alia, stability to the fracture within the bone until it heals, thus, avoiding the pitfalls of vertebroplasty and kyphoplasty. Moreover, in certain embodiments, the IRFD allows the use of Bone Morphogenetic Proteins (BMP) to promote the healing of the fracture and the preservation of function. See, e.g., Rose, et al., supra.

Current alternatives to treat bone fractures, e.g., VCF, such as vertebroplasty and kyphoplasty, with or without balloons, can in some ways be considered beneficial since they reduce pain and improve a subject's quality of life in the short term. However, regulatory agencies have expressed concerns with the use of cement in or nearby the spine (see, e.g., FDA, P.H.W.N., Complications Related to the Use of Bone Cement and Bone Void Fillers in Treating Compression Fractures of the Spine. 2002) which prompted the FDA to issue a new Guidance Document (see FDA, Clinical Trial Considerations: Vertebral Augmentation Devices to Treat Spinal Insufficiency Fractures. 2004). In addition, institutions such as the Technology Evaluation Center of Blue Cross and Blue Shield have recently criticized Kyphoplasty and Vertebroplasty as not having demonstrated improvement in health outcomes. See, The-Gray Sheet, Blue Cross TEC Critiques Kyphoplasty: Kyphon Trial To Address Concerns, in The Gray Sheet. 2005. p. 16.

Exemplary Uses of IRFD Methods and Devices

In various embodiments, methods of the present invention comprise insertion of an IRFD intramedullarly or otherwise into a bone through an opening created in the cortical bone wall or through an already existing opening in the cortical bone wall (e.g., through a fracture in the bone wall). Openings created are typically done through open or minimally invasive procedures and can be internally guided with the help of a fluoroscope or other similar means that are well known to those of skill in the art.

The implantable IRFDs of the invention, and the methods of their use, do not attempt to create cavities within the interior of the bones in question. Of course, some small areas are opened up within the cancellous interior of the bone due to displacement from entry of the device and slight movements that might be needed to adjust the device once inside the bone. However, larger openings as would be done, e.g., by an inflatable balloon or similar device prior to deposition of bone cement or other traditional procedures are not typical features of the current invention. Thus, in typical embodiments, the space in the cancellous material taken up by the IRFDs and the open space created through compression of cancellous material due to movement/placement of the IRFDs is only marginally larger than the space occupied by the implant itself. In various embodiments, the open space created is, e.g., less than about 2% of cancellous space within the bone, less than about 5% of cancellous space within the bone, less than about 10% of cancellous space within the bone, less than about 15% of cancellous space within the bone, less than about 20% of cancellous space within the bone; or less than about 30% of cancellous space within the bone. In yet other embodiments, a device herein creates an open space that is less than 5%, less than 10%, less than 15%, less than 25%, less than 50%, less than 75%, less than 100%, less than 125%, less than 150%, or less than 200% greater than the space occupied by the device itself. In yet other embodiments, the area occupied by the device together with any open space created is, e.g., less than about 2% of cancellous space within the bone, less than about 5% of cancellous space within the bone, less than about 10% of cancellous space within the bone, less than about 15% of cancellous space within the bone, less than about 20% of cancellous space within the bone; less than about 30% of cancellous space within the bone, less than about 35% of cancellous space within the bone, less than about 40% of cancellous space within the bone, less than about 45% of cancellous space within the bone, or less than about 50% of cancellous space within the bone. Because most of the interior of the bone is left intact with use of the invention, bone healing can occur on its own in typical instances.

The devices of the invention and the methods of their use can serve as reduction tools as well as structural reinforcements and fixation tools. The IRFD acts to push bones, e.g., bones, bone fragments, bone surfaces, surfaces of cortical bones or endplates such as within a vertebra, etc., apart until the best attainable position of the bones is obtained. At such stage, the soft tissues surrounding the fractured bone will be tense, providing additional reduction and stability, a phenomena known as ligamentotaxis. See, Leferink, et al., *Eur. Spine J.,* 2003, 12(3):255-60; Starr, et al., *Spine,* 1992, 17(5):551-7; and, Zhang, *Zhonghua Wai Ke Za Zhi,* 1989, 27(12):726-31, 780. Of course, it will be appreciated that many fracture reductions might require additional reduction capability than that supplied by the devices of the invention. For example, in certain embodiments, additional traction or support (e.g., as supplied by lumbar supports or the like) may be required to fully reduce a particular fracture. Those of skill in the art will be quite familiar with such traditional surgical/treatment practices. Thus, in some embodiments, a fracture is reduced using only the devices herein, in some embodiments a fracture is reduced using the devices herein in conjunction with traditional traction and positioning, and in some embodiments, a fracture is reduced using traditional traction and positioning while the devices herein are used for fixation or stabilization of the bones.

Once an IRFD is inserted into the vertebral body, or other bone, that is fractured or collapsed (or that is susceptible to or in danger of such damage) and in need of intramedullar reduction and/or fixation, the device is oriented to have one of its arms or contact surfaces (see, e.g., flexible blades in FIGS. 2 and 3) orientated toward one bone surface (e.g., endplate or cortical bone), and another of its arms or contact surfaces against another, e.g., opposing, endplate or cortical bone surface. The arms or contact surfaces of the device are then expanded apart from one another until they contact the bone surfaces or until they compress an area of cancellous material between the bone surface and their contact surface enough so that it provides a stable footing for the device against the bone surface. In embodiments comprising an articulated strap or band, the contact surfaces which touch the bones, etc., are typically different areas on the same continuous strap. As the strap is moved to reduce the bones, different areas of the strap can comprise the contact surfaces, e.g., different areas of the strap will contact the bones at different times as the strap is deployed.

In many embodiments, the IRFD will be placed midway between the endplates or cortical bones that are to be reduced/fixed. The device will then be deployed until the desired position of the bones/endplates is obtained and left (either temporarily or permanently) in place to provide structure and support to the bone. Several IRFDs may be necessary to reduce a fracture or provide structural support. Of course, it will be appreciated that such multiple devices can be implanted from any portals accessible, and can be inserted from different orientations from one another. In many embodiments, the RFD will be used with the purpose of reducing and supporting vertebral fractures (e.g., VCFs) and, again, depending on the fracture configuration, two or more devices may be necessary to achieve the desired result. Once more, it is to be emphasized that while many descriptions herein focus on use of the invention in treatment of vertebral injuries such as VCF, the methods and devices herein can be used in treatment of other bones as well, e.g., tibia, etc.

The IRFD can be constructed of any suitable materials including metal and metal alloys (e.g., stainless steel, silver, aluminum, titanium, etc.), plastics (e.g., HDPE, PEEK, etc.), ceramics, biological material, or any combination of these or any other materials such as those used by those of skill in the art in construction and/or use of medical implant devices. Furthermore, bio-absorbable materials can be used to construct the IRFD or it can be coated by, have incorporated into, be impregnated with, or made of, substances or drugs, chemicals, or biological materials that can stimulate bone healing, e.g., Bone Morphogenetic Protein (BMP), or which help in prevention of infection, formation of bio-films, etc. Those of skill in the art will be familiar with the many different metals, composites, compounds, etc. capable of use in construction of medical devices. Also in various embodiments, the devices can comprise one or more coatings/inclusions/additions, which can be one or more of: BMP, hydroxyapatite, hydroxyapatite tricalcium phosphate, silver, a silver containing compound, calcium sulfate, a calcium containing compound, an antibacterial material, an antifungal material, or calcium carbonate. Those of skill in the art will be familiar with these and similar compounds, etc. used in treatment of bone and/or with surgical implants (such as bone screws) and/or with other medical devices.

Additionally, the IRFDs herein can be of various sizes depending upon, e.g., the size of the bones concerned, the number of devices to be used, the composition of the devices, the species, age, and health of the subject, etc. Typical devices are of a size capable of insertion within a bone, e.g., a vertebra, of a subject needing their use. For example, in an exemplary device with a posterior or pedicle placement for use in a vertebra of an adult human of average size, a device of the invention can comprise, e.g., 6 mm in width by 40 mm in length of which about ⅓ will be within bone or outside of the bone and ⅔ will be within cancellous space. An exemplary device for anterior placement in a similar bone could be, e.g., 6 mm by 30 mm of which $9/10^{ths}$ will be inside the vertebral body and $1/10^{th}$ will be within the vertebral wall or on the outside of the bone. Of course, in different embodiments, such dimensions can comprise different amounts, e.g., the width can comprise 1 mm or less, 2 mm or less, 3 mm or less, 4 mm or less, 5 mm or less, 6 mm or less, 7 mm or less, 8 mm or less, 9 mm or less, 10 mm or less, or 15 mm or less, etc., and the length can comprise, e.g., 5 mm or less, 10 mm or less, 15 mm or less, 20 mm or less, 25 mm or less, 30 mm or less, 35 mm or less, 40 mm or less, 45 mm or less, 50 mm or less, 55 mm or less, 60 mm or less, 65 mm or less, 70 mm or less, 75 mm or less, 80 mm or less, 85 mm or less, 90 mm or less, 95 mm or less, or 100 mm or less, etc. Furthermore, in such exemplary embodiments, the "closed" height of a device can comprise, e.g., 15 mm or less, 10 mm or less, 9 mm or less, 8 mm or less, 7 mm or less, 6 mm or less, 5 mm or less, 4 mm or less, 6 mm or 6.5 mm. Also, the "open" height of such devices can comprise, e.g., 50 mm or less, 40 mm or less, 35 mm or less, 30 mm or less, 25 mm or less, 20 mm or less, 15 mm or less, or 10 mm or less. Additionally, depending upon, e.g., the particular bone, bone shape, thickness of bone wall, etc., various lengths of the devices can remain within a cortical bone wall, and different lengths can be within the cancellous area, e.g., 10% or less within the bone wall, 20% or less within the bone wall, 30% or less within the bone wall, 40% or less within the bone wall, 50% or less within the bone wall, 60% or less within the bone wall, 70% or less within the bone wall, 80% or less within the bone wall, or 90% or less within the bone wall. In certain embodiments for use in vertebra, pedicle placement devices optionally are longer than those for anterior placement. In some embodiments, the percentage of the device within the bone wall or on the exterior of the bone and the percentage of the device within the cancellous space comprises, e.g., ⅓:⅔ and 1/10:9/10 for pedicle and anterior placement respectively. Again, it will be appreciated that the devices herein can be of various sizes, e.g., smaller for use in smaller sized bones than the examples above, or larger for use in larger sized bones within the same subject. Also, since subjects are of different sizes (e.g., due to different age, gender, species, etc.) the devices can comprise the appropriate size for that particular bone, etc.

In many embodiments, the IRFD will not be removed once the bone surfaces are reduced to the desired location, but will be kept in place until fracture healing is obtained and, if removal is not indicated, will remain in place. Again, additional measures can be taken to promote fracture healing such as bone grafting, injection of Bone Morphogenetic Protein, etc., which can speed the process. In yet other embodiments, the devices herein can be used as reduction tools which may be removed at any time either before or after bone healing has occurred. In various embodiments the devices can have a handle or other option to facilitate the activation of insertion and/or removal. See below. Additionally, in some embodiments, the devices can be used solely as fixation tools with reduction being accomplished by, e.g., traditional surgical techniques such as traction, etc.

Various exemplary embodiments of IRFDs used in the methods herein are shown in the accompanying figures. It should be emphasized that such examples are to be taken as illustration and are not necessarily to be taken as limiting unless specified to be so. Also, as will be appreciated, while some aspects of various embodiments of the devices differ between, e.g., pedicle placement vertebra devices, anterior placement vertebra devices, tibia devices, etc., the various features mentioned in this section and throughout the application can be present in any or all of the various embodiments. Thus, even though an aspect may only be described in its use with an anterior placement vertebra device does not necessarily limit its presence to only such embodiments unless specifically stated so. For example, a curved head or cap is presented in FIG. 1B, however, curved heads or caps (optionally of different curve, etc.) are also possible with devices similar to that shown in FIG. 1A.

Figure 1B:
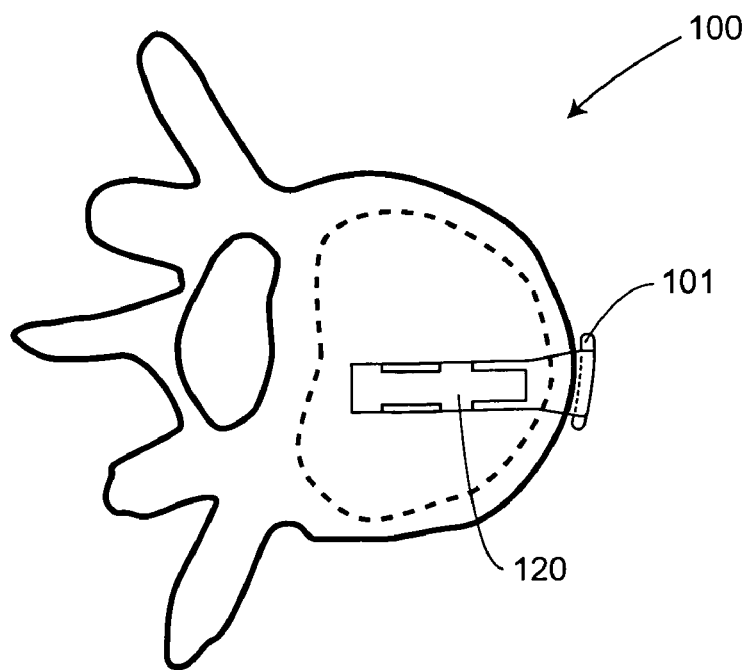

FIG. 1 illustrates various embodiments and positioning of exemplary devices of the invention within vertebra 100. In FIG. 1A, IRFD 110, enters the intramedullary space through insertion through the pedicle of a vertebra. In various embodiments, a percentage, e.g., about $1/3^{rd}$, of the IRFD stays within the pedicle of the vertebra or outside of the vertebra, while about, e.g., $2/3^{rds}$, of the IRFD enters in the cancellous tissue within the vertebral body. In some embodiments, a head area can keep the IRFD from rotating and coming unlodged from its insertion. In FIG. 1B, IRFD 120 enters into the vertebra through the anterior portion of the bone opposite the pedicle side. The embodiment in FIG. 1B shares many similarities to that in FIG. 1A. However, as will be appreciated, different embodiments of the invention can vary in construction, placement, number, etc. For example, a head area can vary between embodiments. In embodiments inserted through a pedicle, for instance, a larger head can be used, while in IRFDs inserted opposite the pedicle a smaller head can be used in order to cause less of a possibility of damage to overlaying tissue. Also, pedicle placement devices can optionally comprise longer lengths than those used in anterior placement. Because of differences in cortical bone thickness, pedicle placement devices can optionally comprise a greater percentage of the device body within the bone itself (as opposed to within the cancellous space). Additionally, an IRFD inserted through the pedicle, typically (but not necessarily exclusively) uses screw threads whereas an IRFD to be inserted anteriorly typically (but not necessarily exclusively) uses a rack/ratchet and pawl (s) to achieve its position within the bone. For example, devices comprising pawl mechanisms can optionally be used in situations wherein the bone wall it is to be inserted into is thin, since the portion of the device within the bone and exterior to the bone is often less than that in typical screw mechanism devices. See below.

In the various embodiments, the holes used for insertion of the IRFD can be, e.g., drilled or cut within the bone. Of course, it is often beneficial to make such holes as small as possible in order to minimize additional damage to the bone. Thus, such holes can be from about 4 mm to about 20 mm in diameter; from about 4 mm to about 15 mm in diameter; from about 4 mm to about 10 mm in diameter; from about 5 mm to about 8 mm in diameter; from about 5.5 mm to about 6.5 mm in diameter; or about 6 mm in diameter or any other desired size (e.g., 1 mm or less, 2 mm or less, 3 mm or less, 4 mm or less, 5 mm or less, 6 mm or less, 7 mm or less, 8 mm or less, 9 mm or less, 10 mm or less, 15 mm or less, 20 mm or less, 25 mm or less, or 30 mm or less. In other embodiments, the devices can be inserted through fractures, breaks, or other non-manmade openings in the bones. In yet other embodiments, such existing fractures/breaks/openings within the bone can be further enlarged and/or shaped to allow insertion of the IRFD. As explained further below, openings within the cortical bone, whatever their origin, can be patterned to aid in stability of the devices. Also, in some embodiments, as explained below, fins/keels can comprise sharp edges which can cut into the bone when the devices are inserted.

It will be appreciated that the IRFDs of the invention can be positioned within bones in a manner so as to best support the bone surfaces, e.g., in terms of leverage, etc. Thus, in usages comprising vertebral bodies, the IRFD can be placed so that support is given near the anterior portion of the vertebra, if that is where the fracture or risk of fracture is, etc. In some embodiments, multiple IRFDs can be placed within a single bone.

In typical devices herein, the edges (those present on the exterior and/or those present on the interior of the bone) of the devices can comprise rounded, blunt, or non-sharp edges in order to help prevent damage to tissue within the subject. See, e.g., FIGS. 1B, 3B, and 3D. In certain embodiments, only some features of the devices comprise rounded or blunt edges, e.g., head/cap regions, those on the exterior of the bone surface, etc. Also, in some embodiments, the portions of the devices on the exterior of the bone surfaces are shaped to fit the contours of the bone on which they rest, thus, presenting a less intrusive profile. Such anatomical shaping can be especially helpful for devices used in anterior placement on vertebra due to the proximity of damageable soft tissue. Such conformation to the bone surface can also aid in preventing the device from slipping or rotating since the mating of the curved surface of the device to the curved surface of the bone will prevent unwanted rotation.

FIG. 2, Panels A-D illustrates other exemplary embodiments of the invention. FIGS. 2A and 2C show sample pedicle versions of the IRFD within a vertebra. The device in 2A is "closed," while the device in 2C is "open." In other words, the device in 2A has been inserted into a bone, but the contact surfaces of the blades have not been moved away from one another in order to contact the bone surfaces, while in FIG. 2C they have been. FIG. 2B shows an exemplary "head" or "cap" area which is present on the exterior surface of the bone used to cover the end of the extender tube and to optionally help keep the IRFD properly adjusted. Additionally, as explained below for anteriorly placed embodiments, "fins" or "keels" such as those illustrated in FIGS. 3G-I can aid in stabilization of the IRFD. See below. FIG. 2D shows a cross-section of the hinged crossbar of an opened IRFD.

Figure 2A:
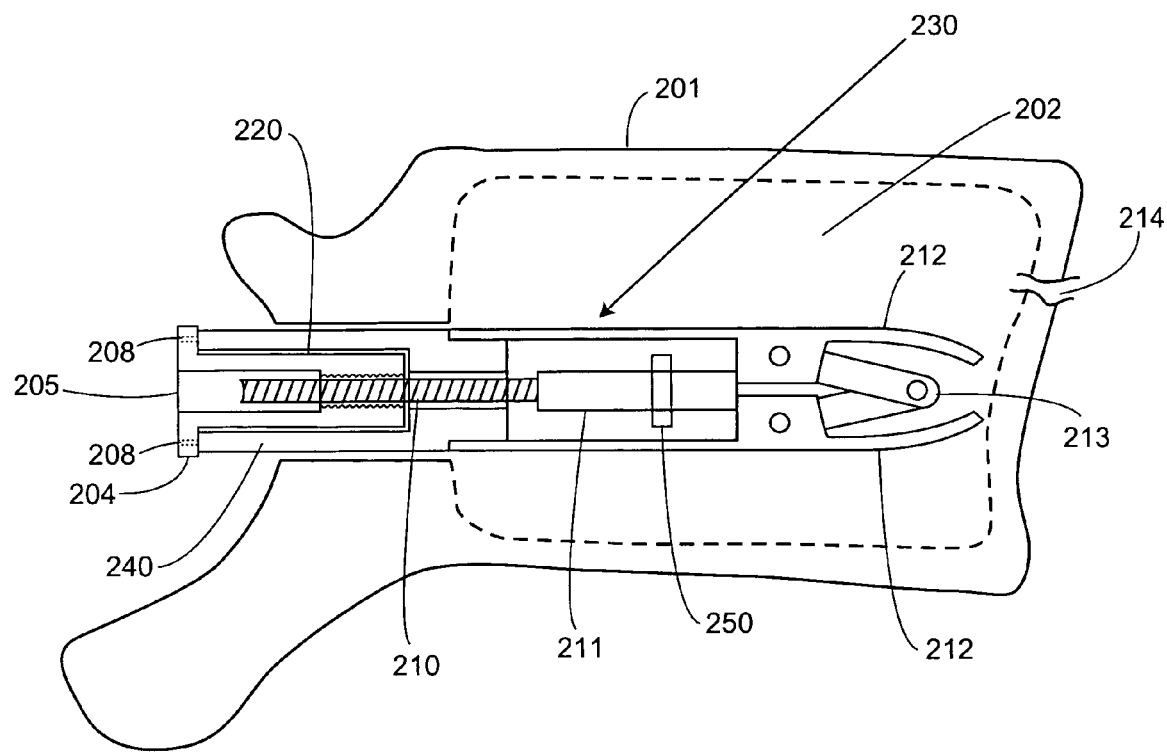
FIG. 2, Panels A-D, shows diagrams of exemplary pedicle placement IRFDs of the invention.

In FIG. 2A, fracture 214, can be seen in vertebra 201. IRFD 230, is shown placed within the vertebra via a hole/opening in the pedicle and extending into cancellous space 202 within the bone. The Figures herein (and in FIGS. 3 and 4) show partial cut-away views of the IRFDs, e.g., the hollow extender tubes and rotators if present are shown cut away to illustrate the interior workings of the devices. As stated previously, the IRFD in FIG. 2A is "closed." That is, the device has not been manipulated to come into contact with (and thereby reduce and/or fix) the bone surfaces of the vertebra. In FIG. 2A, the bone surfaces are the surfaces of the endplates of the vertebra, two endplates facing the medullar cavity (which the IRFD will contact) and two facing the inter-vertebral discs (i.e., on the exterior of the bone).

In exemplary IRFD 230, extension rod 211 traverses through the lumen of hollow extender tube 240. Extender tubes are typically cylindrical, but can also optionally comprise other profiles, e.g., square, rectangular, etc. In this example, extension rod 211 comprises screw 210, used to manipulate the extension rod. In this embodiment, the extension rod traverses through the hollow extender tube connecting to head 204 via rotator 220. The extension rod is attached to hinged crossbar 213, which is, in turn, attached at each of its ends to flexible blades 212 (see pivot points 256 in FIG. 2C). The arms of the hinged crossbar optionally can both be on the same side of the extension rod to which they attach or optionally the arms can be on opposite sides of the extension rod to which they attach (see, e.g., FIG. 2D). The IRFD is optionally helped to stay in place by anchor/anti-rotation fins or keels which in typical embodiments are present on the exterior of the hollow extender tube in the region that would be within the cortical bone. See below, for additional description of fins/keels.

As seen in FIG. 2A, certain embodiments can comprise rotator 220. The rotator comprises a threaded lumen through which extends the screw portion of the extension rod. To move the blades of the device, the rotator is turned. This action causes the rotator to twist around the non-rotating screw of the extension rod, thereby, pulling/pushing the screw and the extension rod and thereby moving the blades. It will be appreciated that in different embodiments, rotators can comprise different constructions or arrangements. For example, in some embodiments, the rotator is simply a hex nut, wing nut or the like which can be twisted around the screw portion of the extension rod, thereby moving the rod in or out and thus moving the hinged crossbar and the flexible blades. In yet other embodiments, the rotator can comprise a device such as that shown in FIG. 2A (e.g., presenting a "U" shaped cross-sectional profile). The depth and shape of the rotator, the length of the rotator that is threaded to accept the screw, and the way the rotator are turned are all optionally varied in different embodiments. The rotator can be turned, e.g., via any appropriate methods, depending upon, e.g., the format of the rotator. Thus, if the rotator comprises a hex nut, it can be turned via a socket wrench or hex nut wrench, etc. Additional exemplary methods of turning the rotator are described below in description of the cap/head area. The rotator can be attached to the head (i.e., the rotator and head/cap can be separate pieces) or optionally can be a continuous piece with the head (see FIG. 2A). Attachments (such as screws, pins, bolts, etc.) between the head/cap (and thus the rotator) and the extender tube (e.g., 208) can help keep the rotator from rotating once the desired alignment of the blades is reached, etc. Some embodiments optionally do not comprise a head/cap, but rather have the end of the extender tube open, allowing access to the rotator.

Figure 2B:
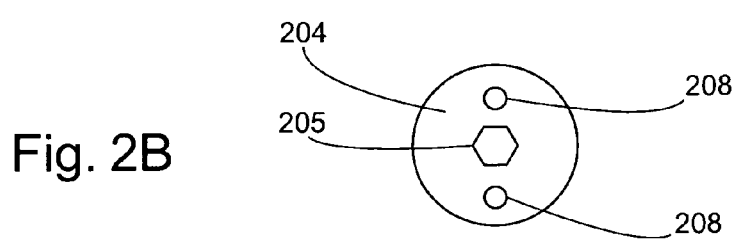

FIG. 2B shows an exemplary end view of head/cap 204, anchoring points 208, and rotator access 205. Anchoring points can comprise, e.g., openings for screws, pins, bolts, etc., which can be threaded depending on the types of anchoring used. It will be appreciated that an anchoring point in a head/cap will optionally have a corresponding anchoring point in the piece the head/cap is intended to attach to. In some embodiments the rotator, extender tube, and head/cap can each comprise different numbers of anchoring or attachment points, while in other embodiments they can comprise the same number of anchoring points in each (e.g., 5 anchoring/attachment points in the head/cap and 5 corresponding points in the extender tube). In some embodiments not all anchoring/attachment points will be utilized in all uses, no matter the number present, while in other embodiments/uses all anchoring/attachment points will optionally be utilized. Various embodiments can comprise different arrangements and number of anchoring points attaching the head to the extender tube (and/or optionally to the rotator). In some embodiments, the anchoring points are optionally used to turn the rotator. Thus, for example, a turning fork comprising a "U" shaped end can fit, one prong into each hole which comprises the anchoring points, and turned to rotate the rotator. Additionally, different embodiments can comprise different number, size, and shape of rotator accesses (e.g., for screw drivers, alien wrenches, rods, etc.). Thus, for example, in FIG. 2B a hexagonal rod, e.g., an alien wrench, can be inserted into rotator access 205 and turned, thus, rotating the rotator. Again, various embodiments can comprise different sizes of rotator access areas, different shapes of rotator access (e.g., square, cross-shaped, etc.). In some embodiments, the rotator access is not an opening, but rather the head/cap completely covers/encloses the end of the rotator. In such embodiments, the rotator access can comprise, e.g., grooves, slots, indentations, etc., for such turning mechanisms as screwdrivers (either flat headed or Phillips headed), etc. For embodiments wherein the rotator and the head are separate pieces, additional attachments can exist between the head/cap and the rotator. Stop plate 250 in FIG. 2A and 270 in FIG. 2B prevents the extension rod from being pulled too far out (e.g., overextending the flexible blades, etc.).

Figure 2C:
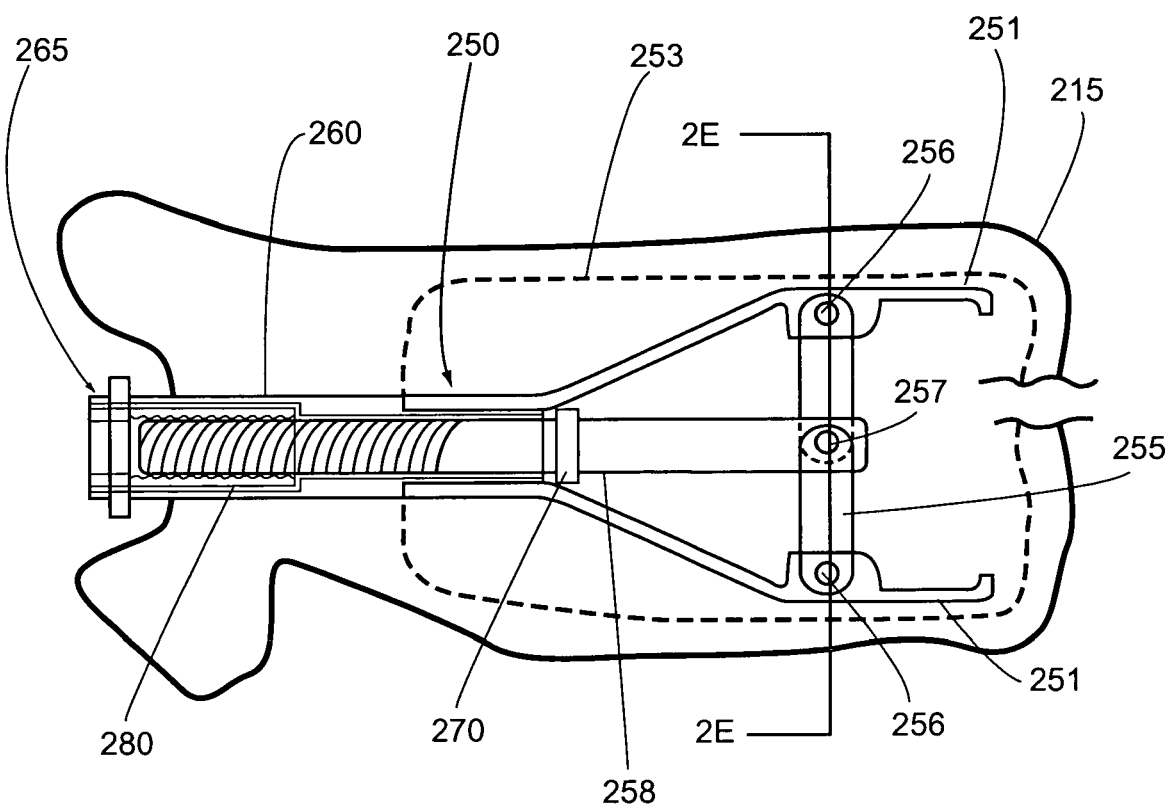

FIG. 2C displays exemplary IRFD 250, similar to that shown in 2A, but with the device "open." As can be seen in 2C, flexible blades 251, are open and have been pushed away from one another so as to come into contact with bone surfaces 253 (the inner surfaces of the vertebral endplates). The flexible blades are moved and held apart by hinged crossbar 255, which attaches to the blades at pivot points 256. The hinged crossbar also has attachment point 257, with extension rod 258. The extension rod, which in this embodiment comprises a screw mechanism, traverses through extender tube 260, and through threaded rotator 280. Head/cap 265 is present on the outside of the bone. Head/cap 265, can be locked in place by using holes and screws, bolts, etc. similar to the device in FIG. 2A. The head/cap can optionally cover the end of the screw, optionally with access to the rotator in order to manipulate the rotator in order to move the extension rod and hence open/close the blades.

Figure 2D:
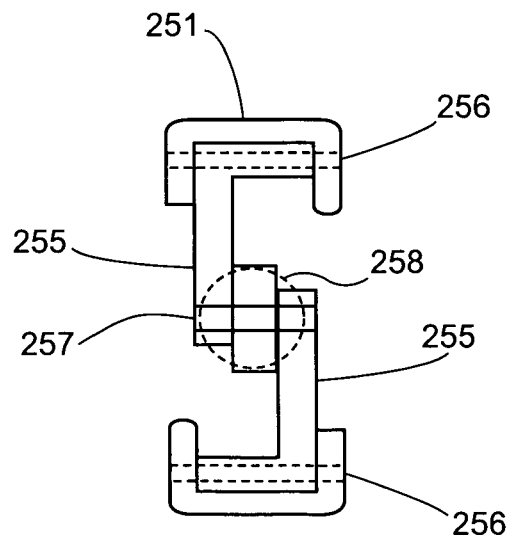

FIG. 2D shows a cross section through the hinged crossbar and flexible blades as shown in FIG. 2C with end outline 258 showing the round outline of the screw portion of the extension rod. Such extension rod can change its cross-sectional profile along its length, e.g., round during the screw portion changing to flat bladed near the hinged cross bar. Thus, as can be seen in FIG. 2D, the extension rod is round in a proximal region, but is flat (or rectangular) in a distal region. Such change and area of change can vary amongst embodiments.

As will be appreciated from FIG. 2, the IRFD of the invention can comprise various configurations in different embodiments. For example, the hinged crossbar as shown in FIG. 2A is hinged towards the anterior of the vertebra (i.e., the hinge when the crossbar is not extended, points towards the anterior of the vertebra), thus, to open the crossbar and extend the flexible blades, the extension rod would be moved back towards the opening in the pedicle. However, it will be appreciated that other embodiments can comprise hinges that are pointed to the posterior of the bone when closed (i.e., the hinge will be towards the pedicle), and thus to open the crossbar and extend the flexible blades, the extension rod is moved in towards the anterior of the vertebra. Additionally, as shown in the various panels of FIG. 2, size of the devices of the invention can vary, as well as can the proportions of the device (e.g., the length of the extension rod versus the flexible blades, the length of the screw portion of the extension rod, the diameter of the screw, the pitch of the screw, where and for what distance the rotator is threaded to engage the screw, what comprises the rotator (e.g., hex nut, cylindrical device similar to FIG. 2A, etc.). As will also be appreciated, the access to the rotator, the screw types, and ways of turning the rotator can vary between embodiments. Thus, in some embodiments, the screw end can be set within an open (but capped) rotator within the extender tube, while in other embodiments, the screw end can extend to the end of the extender tube. Also, the head/cap ends of the devices on the exterior of the bone can be of various configurations. Thus in some embodiments, the head ends can comprise multiple anchor points (e.g., for pins, screws, bolts, etc. to hold the head/cap on to the extender tube and/or to the rotator), can comprise different openings to allow access to the screw end or to turn the rotator (e.g., different sized or shaped openings or indentations, etc.). The pins, screws, etc. used in the anchoring/attachments between the head/cap, rotator, and extender tube are optionally magnetic. In some embodiments, the devices can comprise not heads as in FIG. 2A, but rather comprise the end of the extender tube present on the exterior of the bone allowing access to manipulate the rotator. Also, in various embodiments, various amounts of the device can extend beyond the surface of the exterior of the bone into which it is set. However, in certain embodiments, it is usually desired to have as little as possible of the device protruding from the bone surface in order to minimize damage to overlying tissue. Thus, in actual use, the devices in FIG. 2 would optionally have their head ends against, or near, the exterior bone surfaces. As mentioned previously, the portions of the devices which are present on the exterior of the bone, can be rounded and anatomically shaped to fit the bone surface to minimize tissue damage and help in preventing unwanted movement of the device.

FIG. 3, panels A-I illustrates another exemplary IRFD. The device in FIG. 3 is shown as inserted through the anterior or side of vertebra 300 as opposed to entry through a pedicle as in FIG. 2. Again, such openings in the bone can be through breaks or fractures within the bone, such as break 305, through man-made openings within the bone, or through breaks/fractures in the bone that are enlarged or shaped by a surgeon, etc.

In FIG. 3, IRFD 315 comprises extension rod 317, which uses toothed ratchets rather than the screw mechanism shown in the embodiment in FIG. 2. The extension rod has ratchet teeth on two opposing sides, while the other two sides (which also oppose each other) are smooth or flattened, rather than ratcheted. Thus, the presentation in FIG. 3 shows a profile view (and partial cut away view of the extender tube) of the ratchet side of the extension rod. The side facing the viewer and its opposite side are smooth or non-ratcheted. The extension rod can be of different cross-sectional profiles in different embodiments, e.g., round, hexagonal, etc., but is of a shape which allows turning of the rod and engagement/disengagement of the pawls, e.g., as described below. Each flexible blade 310 comprises pawl 304, which fits into the ratchet teeth. The extension rod is attached, via keyhole slot 312, (or other similar mechanism, e.g., screw mount, bayonet mount, etc.) to removable rod section 320, which has end head 301 on the exterior of the bone.

To open the flexible blades and move them away from one another in order to contact the bone surfaces, thereby reducing and optionally fixing them, the end head is levered, pulled, or pushed away from anchoring plate 303. Those of skill in the art will be familiar with various tools and medical devices, e.g., expanders, levers, etc., which are optionally be used to move end head 301 away from anchoring plate 303. The movement of the end head manipulates the removable rod and thus the ratcheted extension rod, pulling it out of the interior of the bone (or pushing it into the interior of the bone depending on which direction the hinged crossbar points). As the extension rod is moved, it moves hinged crossbar 311, thereby opening or closing the IRFD (i.e., moving the flexible blades away from or towards one another). As the blades are moved apart, the pawls of the flexible blades click into the teeth of the ratchet and keep the blades from collapsing back closed. It will be appreciated that the ratchet mechanism can lock the blades apart at varying positions, thus, the blades do not have to open to their fullest positions in different applications. Different embodiments can comprise different numbers of ratchet teeth per unit length of the extension rod, thus, allowing different levels of control or fine tuning the amount of opening between the flexible blades. For example, a greater number of teeth per unit length can allow a greater number of gradations of opening of the blades, and vice versa. Once the blades are in the desired position, the exterior section of the extension rod (i.e., removable rod 320) can be removed, e.g., by rotation of such exterior section in order to disengage the removable rod at the location of the keyhole slot (or other similar mechanism), such as that shown in FIG. 3C, etc.

Figure 3A:
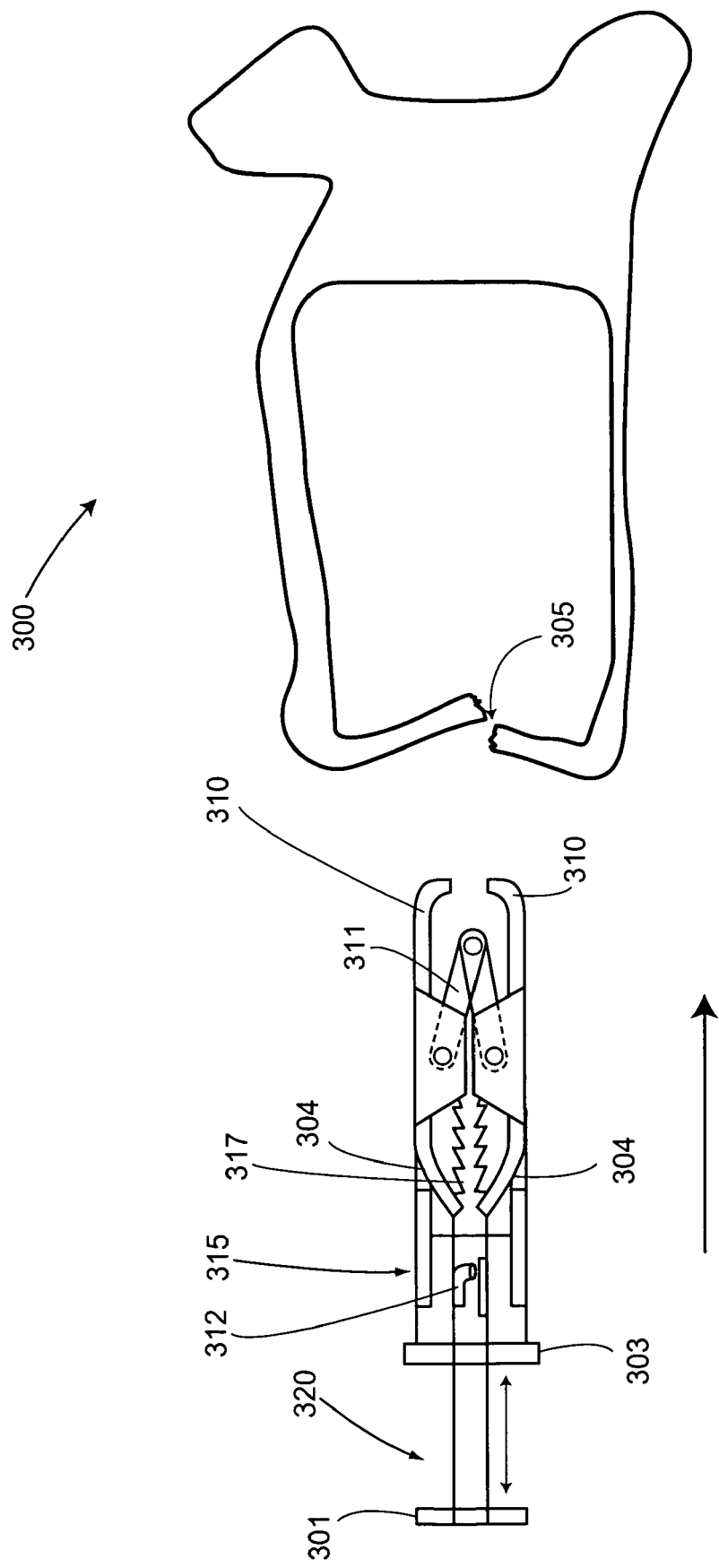
FIG. 3, Panels A-I, shows diagrams of an exemplary anterior placement IRFD of the invention and orientation of such device within a vertebra.

In order to remove the IRFD from the bone, the removable rod can be reinserted and rotated to engage the keyhole slot or other actuator mechanism and the ratcheted portion of the extension rod can be rotated 90 degrees (or optionally more than or less than 90 degrees depending upon, e.g., the width of the ratchet teeth in relation to the size/shape of the extension rod and the pawls, the length of slots on the keyhole device, etc.) so that the pawls no longer mesh into the teeth of the ratchet, but rather encounter the flat sides or areas of the extension rod. Therefore, the flexible blades are no longer locked into position and the blades can be drawn closed by moving (pushing or pulling depending on the direction of the hinged crossbar) the extension rod via the removable rod thus allowing the entire IRFD to be removed from the bone. FIG. 3F shows a top enlarged view of pawl 304, on flexible blade 310.

Figure 3B:
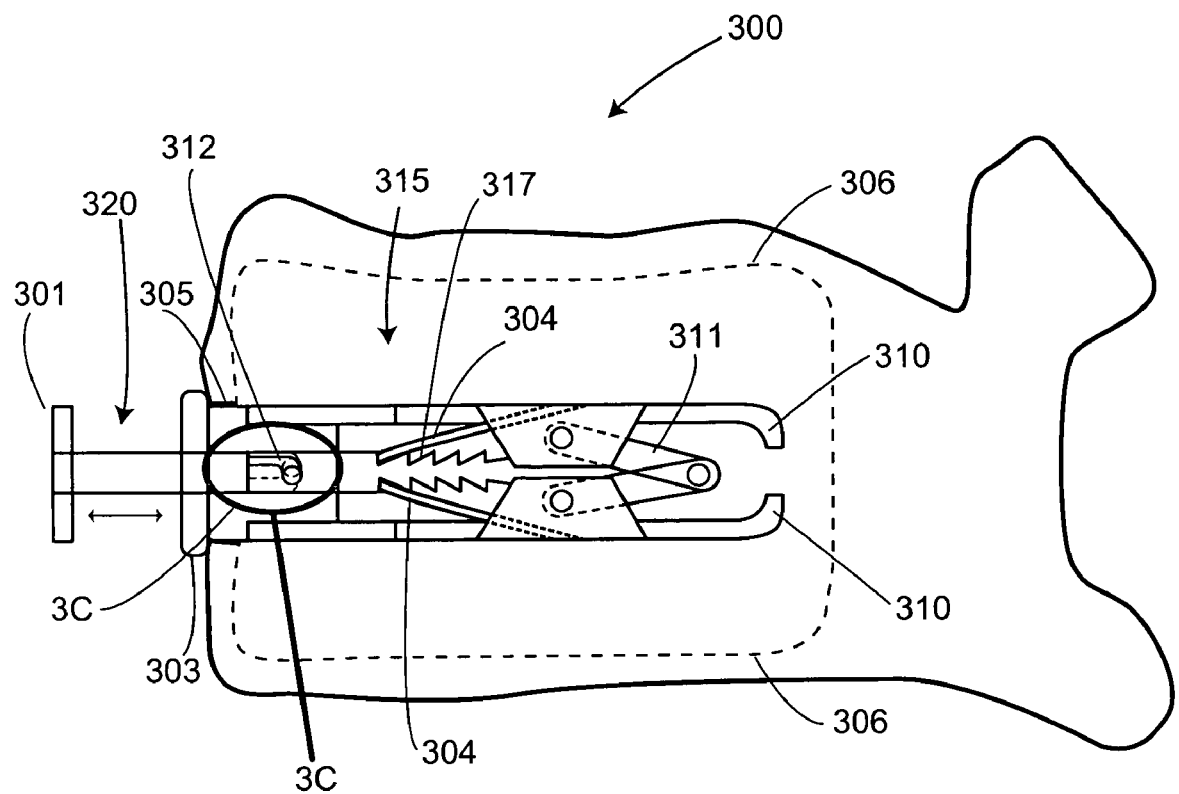

FIG. 3B shows exemplary anterior placement of IRFD 315 inserted into vertebra 300 through fracture 305 (which can be enlarged and/or shaped by a surgeon inserting the device), with the device is in the "closed" position. FIG. 3D shows the device in cancellous space in the "open" position with the blades moved away from one another and contacting inner surfaces 306 of the vertebra endplates.

Figure 3C:
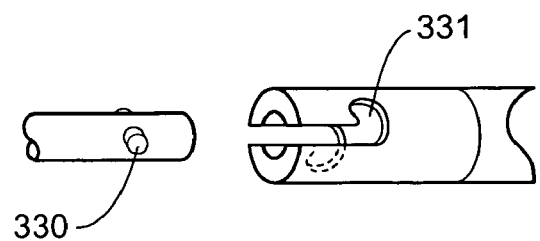
Figure 3D:
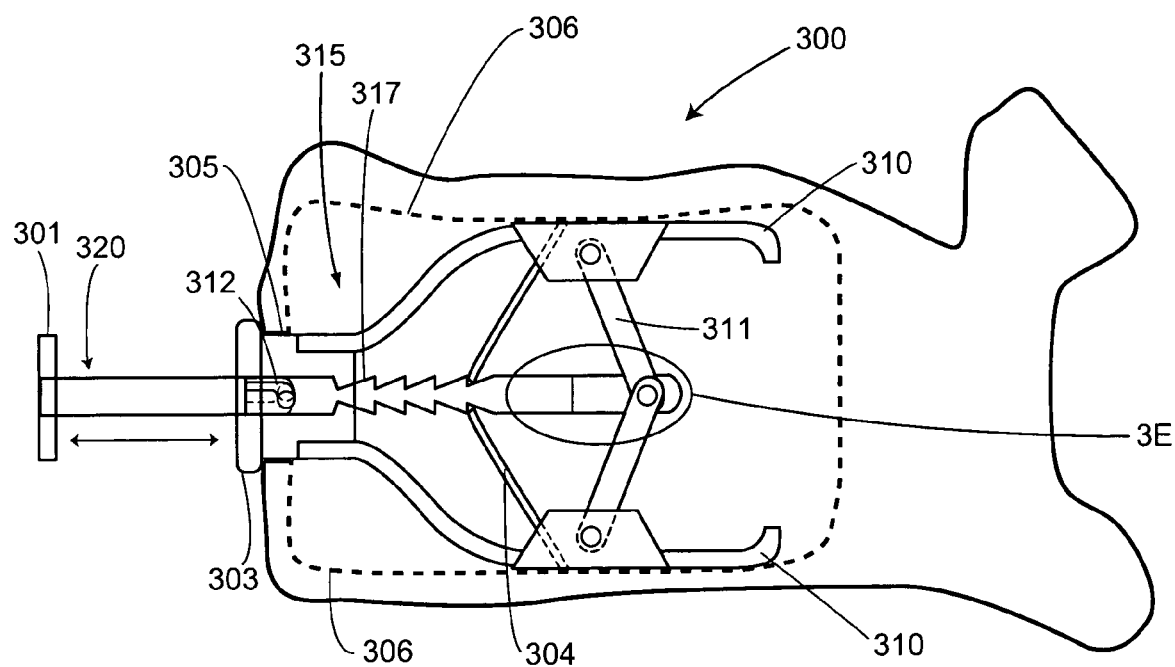

FIG. 3C shows an exemplary actuator mechanism (here a keyhole slot) which allows removable rod 320 to be removed/attached to the rest of the extension rod of the device. It will be appreciated that different embodiments can optionally comprise different actuator mechanisms than that shown in FIG. 3C, e.g., screw mechanisms, etc. In FIG. 3C, the end of removable rod 320 comprises pins 330 which fit into slots 331 present on the end of extension rod 317. When the IRFD is inserted into the bone, the removable rod is attached via the keyhole mechanism to the extension rod (which comprises the ratchet teeth, etc.). After the IRFD is opened, the removable rod can be rotated (either clockwise or counterclockwise depending upon orientation of slots 331) and pulled out. If the IRFD is to be removed from the bone, the removable rod can be reinserted, rotated appropriately, and used to rotate the toothed extension rod. When the toothed extension rod is rotated, the ratcheted sides move and thus release the pawls, which allows the assembly to be collapsed and withdrawn from the subject. The end of the removable rod is of a diameter such that it inserts within its mating end within the extension rod. In different embodiments, both the removable rod section and the toothed extension rod can be of different diameters, but typically the removable rod will fit inside at the end portion of the extension rod. The pins on the removable rod can comprise different diameter, lengths, and number (e.g., 1, 2, 3, 4, 5, etc.) in different embodiments. In typical embodiments, the pins will not protrude further than the surface of the exterior of the extension rod when the pins are inserted within the slots. It will be appreciated that the pins can be present on the end of the extension rod and the slots present on the end of the removable section, etc.

Figure 3E:
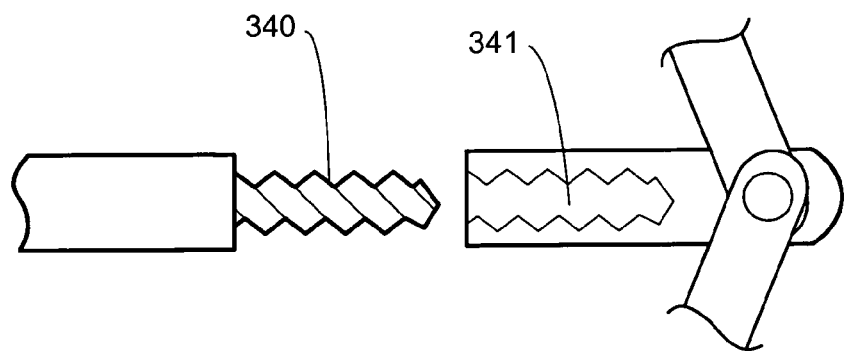
Figure 3F:
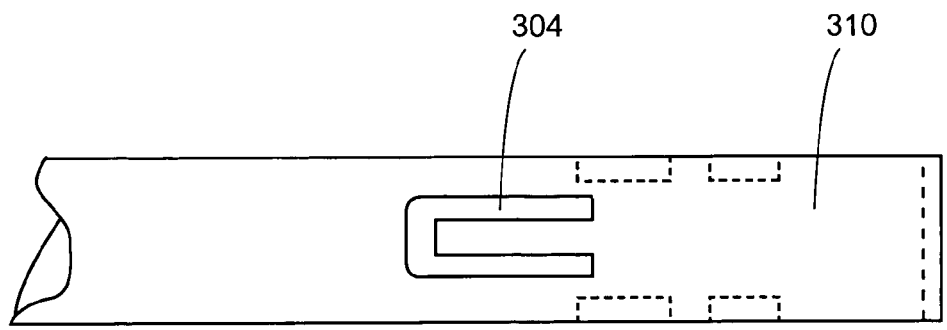

FIG. 3E displays a swivel mechanism which allows ratcheted rod 317 to rotate to disengage the pawls from the ratchet teeth when the IRFD is collapsed prior to removal. Thus, ratcheted extension rod 317 comprises two attached parts, one of which is attached to the hinged cross bar and one of which comprises the ratchet teeth and is attached to the removable rod. The embodiment shown in FIG. 3E comprises a screw mechanism. In different embodiments, the male and female ends can be located on either part of the extension rod. Also, in different embodiments, the screw mechanism can comprise different numbers of threads, different number of threads per unit length, etc. In typical embodiments, the screw is tightened enough so that the two pieces of the extension rod do not come apart when the extension rod is rotated to release the pawls when the device is collapsed to remove from a subject. In yet other embodiments, the swivel mechanism which allows the extension rod to be rotated to release the pawls can comprise a different mechanism than a screw, e.g., a ball joint, etc.

As with the embodiments of FIG. 2, it will be appreciated that the IRFD embodiments of FIG. 3 can comprise various configurations in different embodiments. For example, the hinged crossbar as shown in FIG. 3A is hinged towards the posterior of the vertebra (i.e., the hinge when the crossbar is not extended, points towards the posterior or pedicle side of the vertebra), thus, to open the crossbar and extend the flexible blades, the extension rod would be pulled back towards the opening in the anterior wall. However, it will be appreciated that other embodiments can comprise hinges that are pointed to the anterior of the bone when closed (i.e., the hinge will be away from the pedicle), and thus to open the crossbar and extend the flexible blades, the extension rod is pushed in towards the posterior of the vertebra. Optionally the ratchet teeth can face the opposite direction than that shown in FIG. 3. Additionally, as shown in the various panels of FIG. 3, size of the devices of the invention can vary, as well as can the proportions of the device (e.g., the length of the extension rod versus the flexible blades, etc.). The flexible blades also can vary between the embodiments in terms of their flexibility or stiffness. Additionally, the blades can be flexible over their entire length or can be flexible only over part of their length or can be flexible to varying degrees along their length. As will also be appreciated, the ratchet types (e.g., number of teeth, number of teeth per unit length of the extension rod, slope of the teeth, etc.), the length, curve and amount of pressure of the pawls against the ratchet teeth, the way of manipulating and removing/attaching the removable rod, etc., can all vary between embodiments.

Figure 3G:
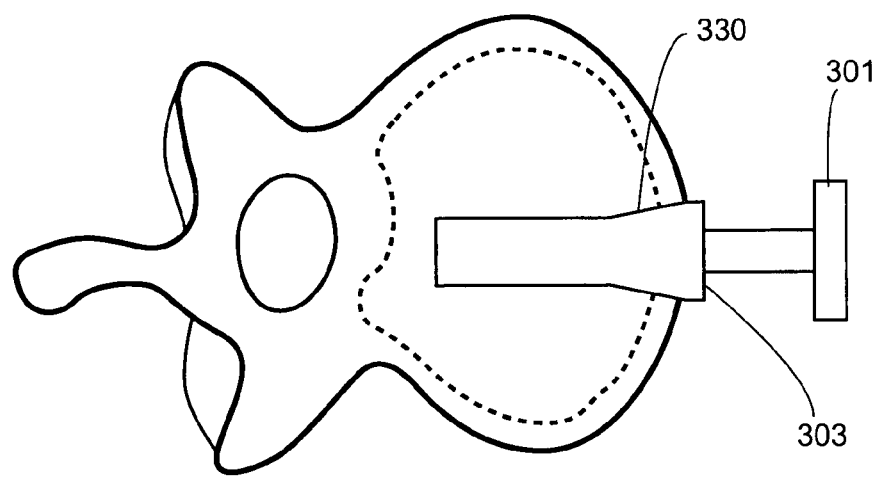
Figure 3H:
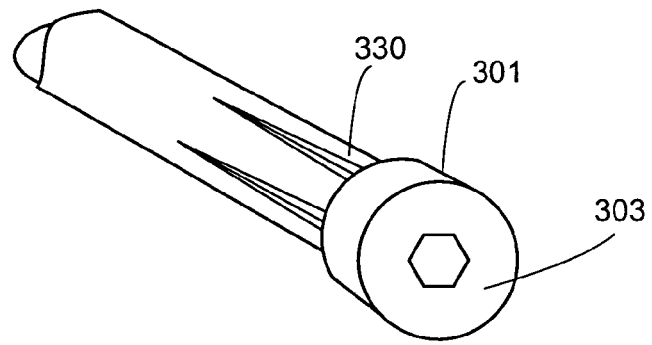
Figure 3I:
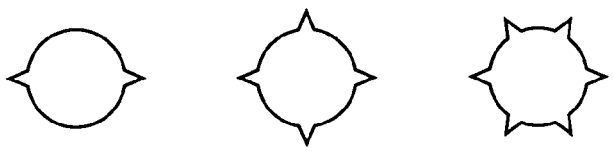

FIGS. 3G-3I, show a view of insertion of an IRFD as in FIG. 3A, showing anti-rotation/stabilizer "fins" or "keels" 330, which can help stabilize the IRFD in the correct placement in the bone. Such fins typically do not extend the entire length of the IRFD, but rather are located on the exterior portion of the extender tube that will be within the cortical bone wall. Thus, in some embodiments, e.g., those in which the bone wall that the IRFD is inserted into is thick, the fins can extend longer along the device than in those embodiments in which the bone into which the device is inserted is thin.

FIG. 3H shows a perspective view of part of the extender tube of an exemplary IRFD showing a number of fins/keels around the circumference of the tube in the area which would come into contact with a cortical bone wall when the device is inserted into a bone. In different embodiments, the number and placement of keels/fins can vary. Thus, some embodiments can comprise 1 fin, 2 fins, 3 fins, 4 fins, 5 fins, or 6 fins or more, etc. See, FIG. 3I. The fins can be equidistant from one another or can be placed in other configurations, e.g., to take advantage of pre-existing fractures in the bone into which it is inserted, etc. In some embodiments, the bone wall into which the fins of the IRFD are to be inserted is shaped (e.g., cut) to allow easier insertion of the finned device. Thus, for example, if an IRFD comprised a round extender tube having 2 equidistant fins, then the bone into which it is to be inserted can be shaped (e.g., cut, drilled, etc.) to include a round shape (of a size allowing insertion of the IRFD) having 2 equidistant cut outs for the fins. Additionally, in some embodiments, including those in which the bone is cut/shaped, the fins themselves are optionally sharp in order to cut into the bone (rather than having the bone cut solely by a different tool) and help in stabilization. In different embodiments, the fins can comprise different slopes, can be of different shapes (which can also vary within the same device) such as points as in FIG. 3I, half circles, squares, etc., and can be of different sharpnesses. In various embodiments, a fin can protrude a distance from the body of the device equal to about that of 1% or less, 2% or less, 3% or less, 4% or less, 5% or less, 6% or less, 7% or less, 8% or less, 9% or less, 10% or less, 15% or less, 20% or less, of the diameter of the device.

Figure 4:
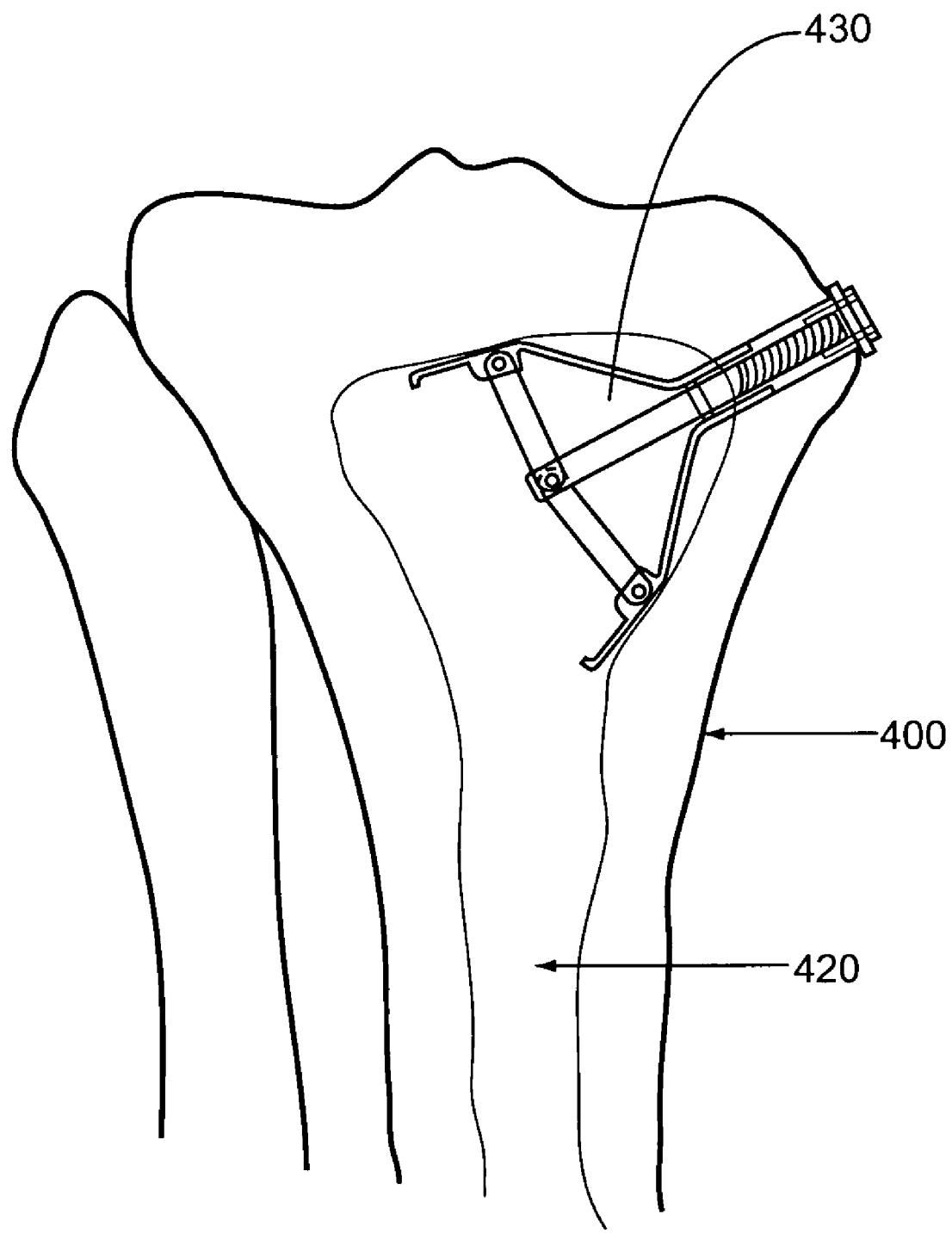
FIG. 4, shows an exemplary tibia placement of an IRFD of the invention.

FIG. 4 displays an example of insertion of exemplary IRFD 430, within tibia 400. As with the above examples with vertebra, the IRFD in FIG. 4 inserts through the cortical bone wall and into cancellous space 420. The device and placement illustrated in FIG. 4 can comprise various embodiments similarly as those described for the various embodiments above.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. A device for reducing and/or fixing one or more bone surfaces at a desired position, the device comprising:
   a) a first flexible blade and a parallel second flexible blade, each blade having a proximal end and a distal end, the proximal end of each blade being directly attached to a hollow extender tube having a lumen;
   b) a hinged two-armed cross bar, one end of which bar is attached to the first blade and one end of which bar is attached to the second blade, wherein the attachments are at points in between the proximal and distal ends of each blade; and,
   c) an extension rod having a proximal end and a distal end, which rod is attached at the distal end to the hinge of the two-armed cross bar and whose proximal end moveably traverses through the lumen of the hollow extender tube; wherein the distal ends of the flexible blades can be moved controllably apart from one another by manipulation of the extension rod, and wherein the flexible blades can be locked at a desired position.

2. The device of claim 1, wherein the blades comprise contact areas which can touch the bone surfaces.

3. The device of claim 2, wherein the bone surfaces are part of one or more bones which bones are anatomically classified as irregular bones, spinal vertebra, or a metaphyseal portion of long bones or flat bones, or a metaphyseal portion of any bone.

4. The device of claim 2, wherein the bone surfaces are cortical bone, endplates, or other bone surfaces capable of sustaining a reduction force.

5. The device of claim 1, wherein the blades comprise rounded or blunt distal ends.

6. The device of claim 1, wherein the blades are flexible over less than their entire length.

7. The device of claim 1, wherein as the extension rod is manipulated it causes the hinged crossbar to move the distal ends of the blades away from one another.

8. The device of claim 1, wherein as the extension rod is manipulated it causes the hinged crossbar to move the distal ends of the blades towards one another.

9. The device of claim 1, wherein the extension rod comprises a screw mechanism.

10. The device of claim 9, further comprising a rotator, which rotator when turned manipulates the screw mechanism of the extension rod which manipulates the hinged crossbar, which thereby moves the distal ends of the flexible blades.

11. The device of claim 1, wherein the extension rod comprises a ratcheted rod, which ratcheted rod comprises a plurality of teeth on two opposing sides and which ratcheted rod also comprises two flattened sides on opposing sides of the rod, wherein the extension rod comprises a swivel mechanism allowing rotation of at least a portion of the proximal end of the extension rod, and wherein each flexible blade comprises a pawl operatively fitted to the teeth on the rod.

12. The device of claim 11, wherein the extension rod is manipulated via a removable rod, thereby moving the hinged cross-bar and thereby moving the distal ends of the flexible blades.

13. The device of claim 1, wherein the device is composed of one or more of:
   HDPE, PEEK, metal, stainless steel, titanium, silver, or plastic.

14. The device of claim 1, wherein the device comprises one or more coatings, which coatings comprise one or more of: Bone Morphogenetic Protein, hydroxyapatite, silver, a silver containing compound, calcium sulfate, a calcium containing compound, an antibacterial material, an antifungal material, or calcium carbonate.

15. The device of claim 1, wherein the device is capable of insertion into one or more bones through openings which comprise one or more holes drilled or cut through cortical bone or a bone wall.

16. The device of claim 15, wherein the holes are from about 4 mm to about 20 mm in diameter; from about 5.5 mm to about 6.5 mm in diameter; or about 6 mm in diameter.

17. The device of claim 1, wherein the device does not create an open space within the medullary cavity of the bone greater than about 2% of cancellous space within the bone, greater than about 5% of cancellous space within the bone, greater than about 10% of cancellous space within the bone, greater than about 15% of cancellous space within the bone, or greater than about 20% of cancellous space within the bone.

18. The device of claim 1, wherein the device does not comprise a balloon or balloon device.

* * * * *